United States Patent
Taratula et al.

(10) Patent No.: US 10,905,766 B2
(45) Date of Patent: Feb. 2, 2021

(54) THERAPEUTIC COMPOSITIONS AND METHODS FOR TREATMENT OF MUSCLE WASTING DISEASES

(71) Applicant: Oregon State University, Corvallis, OR (US)

(72) Inventors: Oleh Taratula, Portland, OR (US); Canan Schumann, Portland, OR (US); Olena Taratula, Portland, OR (US); Adam W. G. Alani, Beaverton, OR (US)

(73) Assignee: Oregon State University, Corvallis, OR (US)

( * ) Notice: Subject to any disclaimer, the term of this patent is extended or adjusted under 35 U.S.C. 154(b) by 288 days.

(21) Appl. No.: 15/984,261

(22) Filed: May 18, 2018

(65) Prior Publication Data

US 2018/0303944 A1    Oct. 25, 2018

Related U.S. Application Data

(60) Provisional application No. 62/475,498, filed on Mar. 23, 2017.

(51) Int. Cl.
| | | |
|---|---|---|
| *A61K 47/34* | (2017.01) | |
| *A61K 48/00* | (2006.01) | |
| *A61K 31/7105* | (2006.01) | |
| *A61K 9/00* | (2006.01) | |
| *C08L 77/04* | (2006.01) | |
| *A61K 45/06* | (2006.01) | |
| *A61K 9/51* | (2006.01) | |
| *A61K 38/17* | (2006.01) | |
| *A61P 21/00* | (2006.01) | |
| *C07K 14/47* | (2006.01) | |

(52) U.S. Cl.
CPC ............ *A61K 47/34* (2013.01); *A61K 9/0019* (2013.01); *A61K 9/51* (2013.01); *A61K 31/7105* (2013.01); *A61K 38/1709* (2013.01); *A61K 45/06* (2013.01); *A61K 48/0058* (2013.01); *C08L 77/04* (2013.01); *A61P 21/00* (2018.01); *C07K 14/473* (2013.01); *C08L 2203/02* (2013.01)

(58) Field of Classification Search
CPC .................................................... A61K 47/34
See application file for complete search history.

(56) References Cited

U.S. PATENT DOCUMENTS

| 8,450,282 B2 | 5/2013 | Kataoka et al. |
| 2016/0185836 A1 | 6/2016 | Kumar et al. |

FOREIGN PATENT DOCUMENTS

| EP | 1859812 B1 | | 1/2014 |
| EP | 3106177 A1 | | 12/2016 |
| WO | WO01/57190 | * | 8/2001 |
| WO | WO 2011/077787 A1 | | 6/2011 |

OTHER PUBLICATIONS

STIC structure search for PEG-(pGUT-DET)2 (Year: 2020).*
Osada et al. (J.R. Soc. Interface. 2009; 6: S325-339). (Year: 2009).*
Itaka et al. (Molecular Therapy vol. 15 No. 9, 1655-1662 Sep. 2007) (Year: 2007).*
Akagi et al. (Gene Therapy (2007) 14, 1029-1038. doi:10.1038/sj.gt.3302945; published online Apr. 26, 2007) (Year: 2007).*
Oregon State University, Treatment for Muscle Atrophy and for Enhancing Muscle Growth, Summary, retrieved from http://oregonstate.technologypublisher.com/tech/Treatment_for_Muscle_Atrophy_and_for_Enhancing_Muscle_Growth on May 18, 2018.
Schumann et al., A Nanoparticle Mediated Approach for the Treatment of Cancer Cachexia via Increasing Lean Muscle Mass in Mice, 2017 AAPS Annual Meeting and Exposition, Abstract, retrieved from https://annual.aapsmeeting.org/event/member/415258 on May 18, 2018.
Schumann et al., A Nanoparticle Mediated Approach for the Treatment of Cancer Cachexia via Increasing Lean Muscle Mass in Mice, 2017 AAPS Annual Meeting and Exposition, Poster.
Barthélémy et al., "Personalized gene and cell therapy for Duchenne Muscular Dystrophy." *Neuromuscular Disorders*, (2018). (Accepted manuscript, 61 pages).
International Search Report and Written Opinion dated Aug. 29, 2018, by the ISA/US acting as International Searching Authority for PCT App. No. PCT/US2018/033540 (12 pages).
Kim et al., "Therapeutic efficacy of a systemically delivered oncolytic adenovirus—biodegradable polymer complex." *Biomaterials*, 34(19): 4622-4631 (2013).
Okuda et al., "Development of biodegradable polycation-based inhalable dry gene powders by spray freeze drying." *Pharmaceutics*, 7(3): 233-254 (2015).
Pittella et al., "Polymeric micelles for siRNA delivery." *RNA Interference from Biology to Therapeutics*, Springer, Boston, MA, pp. 161-184 (2013).

* cited by examiner

*Primary Examiner* — Scott Long
(74) *Attorney, Agent, or Firm* — Klarquist Sparkman, LLP

(57) ABSTRACT mRNA polymer complexes and drug delivery systems are disclosed herein that include a cationic polymer electrostatically complexed to an mRNA molecule that encodes a desired protein. Also disclosed herein are methods of treating as well as methods of slowing the loss of, increasing, and/or maintaining lean muscle mass in a subject, such as using mRNA polymer complexes and drug delivery systems.

20 Claims, 11 Drawing Sheets

Specification includes a Sequence Listing.

Poly Asp(DET)

mRNA

Poly Glu(DET)

mRNA

SEQUENCE LISTING

```
<160> NUMBER OF SEQ ID NOS: 8

<210> SEQ ID NO 1
<211> LENGTH: 344
<212> TYPE: PRT
<213> ORGANISM: Homo sapiens

<400> SEQUENCE: 1

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175
```

-continued

```
Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
            195                 200                 205

Asn Asp Gly Val Thr Tyr Ser Ser Ala Cys His Leu Arg Lys Ala Thr
            210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
            275                 280                 285

Ala Thr Tyr Ala Ser Glu Cys Ala Met Lys Glu Ala Ala Cys Ser Ser
            290                 295                 300

Gly Val Leu Leu Glu Val Lys His Ser Gly Ser Cys Asn Ser Ile Ser
305                 310                 315                 320

Glu Asp Thr Glu Glu Glu Glu Asp Glu Asp Gln Asp Tyr Ser Phe
                325                 330                 335

Pro Ile Ser Ser Ile Leu Glu Trp
            340

<210> SEQ ID NO 2
<211> LENGTH: 315
<212> TYPE: PRT
<213> ORGANISM: Homo sapiens

<400> SEQUENCE: 2

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
            35                  40                  45

Trp Met Ile Phe Asn Gly Gly Ala Pro Asn Cys Ile Pro Cys Lys Glu
50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
            115                 120                 125

Val Gln Tyr Gln Gly Arg Cys Lys Lys Thr Cys Arg Asp Val Phe Cys
            130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
```

```
              195                 200                 205
Lys Cys Ile Lys Ala Lys Ser Cys Glu Asp Ile Gln Cys Thr Gly Gly
            210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
            275                 280                 285

Ser Ile Ser Glu Asp Thr Glu Glu Glu Glu Asp Glu Asp Gln Asp
            290                 295                 300

Tyr Ser Phe Pro Ile Ser Ser Ile Leu Glu Trp
305                 310                 315
```

<210> SEQ ID NO 3
<211> LENGTH: 317
<212> TYPE: PRT
<213> ORGANISM: Homo sapiens

<400> SEQUENCE: 3

```
Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
                20                  25                  30

Trp Leu Arg Gln Ala Lys Asn Gly Arg Cys Gln Val Leu Tyr Lys Thr
            35                  40                  45

Glu Leu Ser Lys Glu Glu Cys Cys Ser Thr Gly Arg Leu Ser Thr Ser
50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
                100                 105                 110

Lys Pro Arg Cys Val Cys Ala Pro Asp Cys Ser Asn Ile Thr Trp Lys
            115                 120                 125

Gly Pro Val Cys Gly Leu Asp Gly Lys Thr Tyr Arg Asn Glu Cys Ala
130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
                180                 185                 190

Asn Arg Ile Cys Pro Glu Pro Ala Ser Ser Glu Gln Tyr Leu Cys Gly
            195                 200                 205

Asn Asp Gly Val Thr Tyr Ser Ser Ala Cys His Leu Arg Lys Ala Thr
            210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255
```

```
Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
            275                 280                 285

Ala Thr Tyr Ala Ser Glu Cys Ala Met Lys Glu Ala Ala Cys Ser Ser
            290                 295                 300

Gly Val Leu Leu Glu Val Lys His Ser Gly Ser Cys Asn
305                 310                 315
```

<210> SEQ ID NO 4
<211> LENGTH: 288
<212> TYPE: PRT
<213> ORGANISM: Homo sapiens

<400> SEQUENCE: 4

```
Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
            35                  40                  45

Trp Met Ile Phe Asn Gly Gly Ala Pro Asn Cys Ile Pro Cys Lys Glu
            50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
            115                 120                 125

Val Gln Tyr Gln Gly Arg Cys Lys Lys Thr Cys Arg Asp Val Phe Cys
            130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
            195                 200                 205

Lys Cys Ile Lys Ala Lys Ser Cys Glu Asp Ile Gln Cys Thr Gly Gly
            210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
            275                 280                 285
```

<210> SEQ ID NO 5
<211> LENGTH: 1032
<212> TYPE: RNA
<213> ORGANISM: Homo sapiens

<400> SEQUENCE: 5

```
augguccgcg cgaggcacca gccgggugggg cuuugccucc ugcugcugcu gcucugccag      60
uucauggagg accgcagugc ccaggcuggg aacugcuggc uccgucaagc gaagaacggc     120
cgcugccagg uccuguacaa gaccgaacug agcaaggagg agugcugcag caccggccgg     180
cugagcaccu cguggaccga ggaggacgug aaugacaaca cacucuucaa guggaugauu     240
uucaacgggg cgcccccaa cugcaucccc uguaaagaaa cgugugagaa cguggacugu     300
ggaccuggga aaaaaugccg aaugaacaag aagaacaaac cccgcugcgu cugcgccccg     360
gauuguucca cauccaccug aaggguccca gucugcgggc uggaugggaa accuaccgc      420
aaugaaugug cacuccuaaa ggcaagaugu aaagagcagc cagaacugga aguccaguac     480
caaggcagau guaaaaagac uugucgggau guuuucuguc caggcagcuc cacaugugug     540
guggaccaga ccaauaaugc cuacugugug accuguaauc ggauuugccc agagccugcu     600
uccucugagc aauaucucug ugggaaugau ggagucaccu acuccagugc ugccaccug      660
agaaaggcua ccugccugcu gggcagaucu auuggauuag ccuaugaggg aaaguguauc     720
aaagcaaagu ccugugaaga uauccagugc acuggugga aaaaauguuu augggauuuc      780
aagguuggga gaggccggug uucccucugu gaugagcugu gcccugacag uaagucggau     840
gagccugucu gugccaguga caaugccacu uaugccagcg agugugccau gaaggaagcu     900
gccugcuccu caggugugcu acuggaagua agcacuccg gaucuugcaa cuccauuucg      960
gaagacaccg aggaagagga ggaagaugaa gaccaggacu acagcuuucc uauaucuucu    1020
auucuagagu gg                                                        1032
```

<210> SEQ ID NO 6
<211> LENGTH: 945
<212> TYPE: DNA
<213> ORGANISM: Homo sapiens

<400> SEQUENCE: 6

```
gggaactgct ggctccgtca agcgaagaac ggccgctgcc aggtcctgta caagaccgaa      60
ctgagcaagg aggagtgctg cagcaccggc cggctgagca cctcgtggac cgaggaggac     120
gtgaatgaca cacactcttt caagtggatg attttcaacg ggcgcccc caactgcatc       180
ccctgtaaag aaacgtgtga aacgtggac tgtggacctg gaaaaaatg ccgaatgaac       240
aagaagaaca acccccgctg cgtctgcgcc ccggattgtt ccacatcac ctggaagggt      300
ccagtctgcg gctggatgg aaaacctac cgcaatgaat gtgcactcct aaaggcaaga      360
tgtaaagagc agccagaact ggaagtccag taccaaggca gatgtaaaaa gacttgtcgg     420
gatgttttct gtccaggcag ctccacatgt gtggtggacc agaccaataa tgcctactgt     480
gtgacctgta atcggatttg cccagagcct gcttcctctg agcaatatct ctgtgggaat     540
gatggagtca cctactccag tgcctgccac ctgagaaagg ctacctgcct gctgggcaga     600
tctattggat tagcctatga gggaaagtgt atcaaagcaa agtcctgtga agatatccag     660
tgcactggtg gaaaaaatg tttatgggat ttcaaggttg ggagaggccg tgttccctc      720
tgtgatgagc tgtgccctga cagtaagtcg gatgagcctg tctgtgccag tgacaatgcc     780
acttatgcca gcgagtgtgc catgaaggaa gctgcctgct cctcaggtgt gctactggaa     840
gtaaagcact ccggatcttg caactccatt tcggaagaca ccgaggaaga ggaggaagat     900
gaagaccagg actacagctt tcctatatct tctattctag agtgg                    945
```

<210> SEQ ID NO 7
<211> LENGTH: 954
<212> TYPE: DNA
<213> ORGANISM: Homo sapiens

<400> SEQUENCE: 7

```
atggtccgcg cgaggcacca gccgggtggg ctttgcctcc tgctgctgct gctctgccag      60
ttcatggagg accgcagtgc ccaggctggg aactgctggc tccgtcaagc gaagaacggc     120
cgctgccagg tcctgtacaa gaccgaactg agcaaggagg agtgctgcag caccggccgg     180
ctgagcacct cgtggaccga ggaggacgtg aatgacaaca cactcttcaa gtggatgatt     240
ttcaacgggg gcgcccccaa ctgcatcccc tgtaaagaaa cgtgtgagaa cgtggactgt     300
ggacctggga aaaatgccg aatgaacaag aagaacaaac cccgctgcgt ctgcgccccg     360
gattgttcca acatcacctg aagggtcca gtctgcgggc tggatgggaa aacctaccgc     420
aatgaatgtg cactcctaaa ggcaagatgt aaagagcagc cagaactgga agtccagtac     480
caaggcagat gtaaaaagac ttgtcgggat gttttctgtc caggcagctc cacatgtgtg     540
gtggaccaga ccaataatgc ctactgtgtg acctgtaatc ggatttgccc agagcctgct     600
tcctctgagc aatatctctg tgggaatgat ggagtcacct actccagtgc ctgccacctg     660
agaaaggcta cctgcctgct gggcagatct attggattag cctatgaggg aaagtgtatc     720
aaagcaaagt cctgtgaaga tatccagtgc actggtggga aaaaatgttt atgggatttc     780
aaggttggga gaggccggtg ttccctctgt gatgagctgt gccctgacag taagtcggat     840
gagcctgtct gtgccagtga caatgccact tatgccagcg agtgtgccat gaaggaagct     900
gcctgctcct caggtgtgct actggaagta aagcactccg gatcttgcaa ctga           954
```

<210> SEQ ID NO 8
<211> LENGTH: 864
<212> TYPE: DNA
<213> ORGANISM: Homo sapiens

<400> SEQUENCE: 8

```
gggaactgct ggctccgtca agcgaagaac ggccgctgcc aggtcctgta caagaccgaa      60
ctgagcaagg aggagtgctg cagcaccggc cggctgagca cctcgtggac cgaggaggac     120
gtgaatgaca cacactcttt caagtggatg attttcaacg gggcgcccc caactgcatc     180
ccctgtaaag aaacgtgtga gaacgtggac tgtggacctg ggaaaaatg ccgaatgaac     240
aagaagaaca accccgctg cgtctgcgcc ccggattgtt ccaacatcac ctggaagggt     300
ccagtctgcg gctggatgg gaaaacctac cgcaatgaat gtgcactcct aaaggcaaga     360
tgtaaagagc agccagaact ggaagtccag taccaaggca gatgtaaaaa gacttgtcgg     420
gatgttttct gtccaggcag ctccacatgt gtggtggacc agaccaataa tgcctactgt     480
gtgacctgta atcggatttg cccagagcct gcttcctctg agcaatatct ctgtgggaat     540
gatggagtca cctactccag tgcctgccac ctgagaaagg ctacctgcct gctgggcaga     600
tctattggat tagcctatga gggaaagtgt atcaaagcaa agtcctgtga agatatccag     660
tgcactggtg ggaaaaaatg tttatgggat ttcaaggttg ggagaggccg gtgttccctc     720
tgtgatgagc tgtgccctga cagtaagtcg gatgagcctg tctgtgccag tgacaatgcc     780
acttatgcca gcgagtgtgc catgaaggaa gctgcctgct cctcaggtgt gctactggaa     840
gtaaagcact ccggatcttg caac                                            864
```

THERAPEUTIC COMPOSITIONS AND METHODS FOR TREATMENT OF MUSCLE WASTING DISEASES

CROSS REFERENCE TO RELATED APPLICATION

This application claims the benefit of U.S. Provisional Application No. 62/475,498, filed on Mar. 23, 2017, which is incorporated by reference herein in its entirety.

FIELD OF THE INVENTION

This disclosure relates to compositions and methods for treating muscle atrophy or muscle wasting diseases, particularly cachexia.

BACKGROUND

Muscle atrophy is a detrimental and often severely debilitating disease state whose etiology lies within a myriad of disease states ranging from AIDS, sepsis, cardiac failure, muscular dystrophies, cancer, and the natural process of aging. The extent to which the atrophy is occurring can be a clear prognostic indicator of patient recovery and survival. Therefore, the ability to maintain healthy lean muscle mass whether through exercise or other therapeutic interventions is crucial for the preservation of mobility during aging, preventing metabolic disorders, and increasing both quality and longevity of life in patients experiencing disease states that promote active muscle wasting. Muscle atrophy/wasting is characterized by a catabolic state coined cachexia, a state of illness involving marked weight and muscle loss, and unfortunately is present in approximately three quarters of cancer patients, ultimately increasing mortality and morbidity. Surprisingly, recent studies and clinical findings have shown that cachexia may be a direct cause of death within the cancer patient population, and, therefore, having the means to stop, slow, or completely reverse muscle atrophy has the potential to increase patient survival.

Muscle atrophy is a process where poor nutrition, fasting, denervation, inactivity, and/or disease states contribute to the induction or repression of a set of genes responsible for muscle atrophy termed "atrogenes." However, in many patient populations, muscle wasting cannot be simply reversed by nutritional support or physical exercise (Gallagher et al. Clin. Cancer Res., 18, 2817-2827, 2012), and, therefore, efficient therapies, that can preserve or increase skeletal muscle mass independent of exercise and special diets, are highly warranted. Two predominant pathways for atrogenes are activated in the presence of a variety of catabolic stimuli resulting in protein destruction and degradation, the ubiquitin-proteasome and autophagy-lysosome systems. The extent of upregulation of each system plays a role in how muscle atrophy will affect the patient. The ubiquitin-proteasome system is the reason that muscle strength is severely diminished during muscle atrophy due to the degradation of myofibrillar components as well as the loss of the contractile machinery needed for muscles to function. Upregulation and activation of the autophagy-lysosome system plays a major role in decreasing muscle endurance capacity via the destruction of mitochondria and other organelles needed for lean muscle mass energy production.

One of the most influential regulators of muscle catabolism via is myostatin, the endogenous inhibitor of muscle growth, which is upregulated in numerous disease states (cancer associated cachexia, diabetes, chronic renal disease, chronic obstructive pulmonary disease, heart failure, and sarcopenia). Myostatin binds to the activin A receptor type IIB (ActRIIB), which activates the myostatin-activin A signaling pathway. This induces muscle atrophy through the inhibition of PI3K-AKT proliferation and activation of SMAD2 and SMAD3, ultimately upregulating the ubiquitin-proteasome system. Both of these downstream signaling events have a profound negative effect on muscle differentiation and hypertrophy. Myostatin has been sought after as a therapeutic treatment option due to the lack of exercise and special dietary requirements normally needed to stimulate muscle growth. Generally, anti-myostatin therapy is provided through administration of anti-myostatin antibodies, solubilized receptors, and solubilized receptor fragments, which neutralize myostatin and, thus, abrogate the hypotrophic effects on muscle tissue.

Follistatin (FS), a secreted glycoprotein and the natural biological antagonist to myostatin, neutralizes circulating myostatin before it can bind to and activate the ActRIIB receptor signaling cascade. As such, it has become an avenue for the treatment of cachexia, having been studied within human and non-human primate models in regards to increasing lean muscle mass. It has been reported that the resulting progeny of a myostatin knockout mouse crossed with a mouse carrying an FS transgene had a quadrupling of lean muscle mass, versus a doubling of lean muscle mass seen in myostatin knockout mouse alone.

In animal models, a viral vector delivery system containing FS cDNA and administered via direct site injections has been used to increase FS. The use of a viral delivery method includes a plethora of potential issues to overcome before becoming a clinically viable option. The limitations associated with viral vector delivery technology includes both the delivery system and the nucleic acid cargo used to produce the protein of interest, such as 1) the use of potent immunosuppressive therapy administered to avoid harmful immune and inflammatory responses associated with the viral delivery system, 2) variable viral clearance and inconsistent follistatin treatment efficacy due to differences in immune responses within each patient, and 3) the potential for permanent genomic insertion of the viral gene therapy cargo.

Therefore, a safe and efficient approach capable of increasing skeletal muscle mass and restricting body fat accumulation is desirable.

SUMMARY

Disclosed herein are mRNA polymer complexes that include a cationic polymer electrostatically complexed to an mRNA molecule that encodes a desired protein. In some examples, the complex includes an mRNA molecule that encodes a follistatin protein. In some examples, the mRNA molecule encodes a follistatin protein having an amino acid sequence at least 95% identical to the amino acid sequence set forth in SEQ ID NO: 1, SEQ ID NO: 2, SEQ ID NO: 3, or SEQ ID NO: 4 and/or the mRNA molecule comprises a nucleic acid sequence at least 85% identical to the nucleic acid sequence set forth in SEQ ID NO: 5, SEQ ID NO: 6, SEQ ID NO: 7, or SEQ ID NO: 8. In some examples, the mRNA molecule encodes a follistatin protein having the amino acid sequence set forth in SEQ ID NO: 1, SEQ ID NO: 2, SEQ ID NO: 3, or SEQ ID NO: 4 and/or the mRNA molecule comprises the nucleic acid sequence set forth in SEQ ID NO: 5, SEQ ID NO: 6, SEQ ID NO: 7, or SEQ ID NO: 8. In some examples, the polymer of the complex includes an aspartic acid DET polymer, for example, an n-butyl poly{N—[N-(2-aminoethyl)aminoethyl]aspartamide} cationic polymer. In some examples, the polymer of the complex includes a poly{N—[N-(2-aminoethyl)aminoethyl]aspartamide} (pASP-DET) comprising poly(aspartamide) (pASP) derivatives bearing diethylenetriamine (DET) side chains.

In some examples, the complex includes a polymer having one of the following formulas:

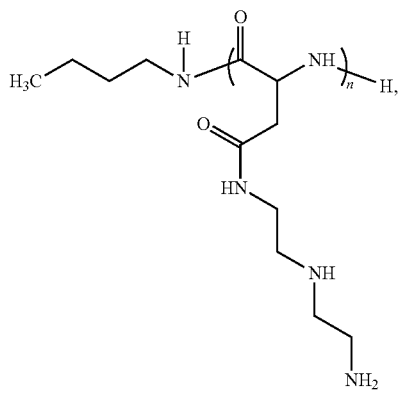

pASP-DET

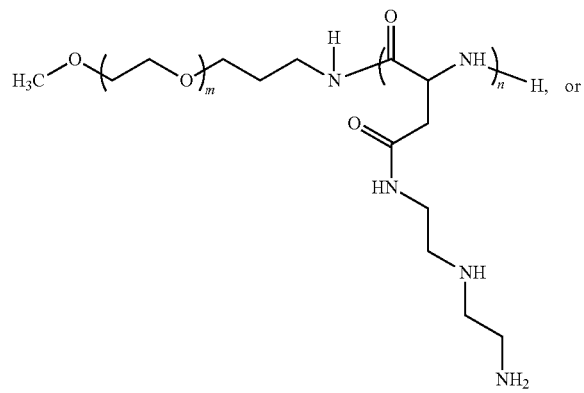

PEG-pASP-DET

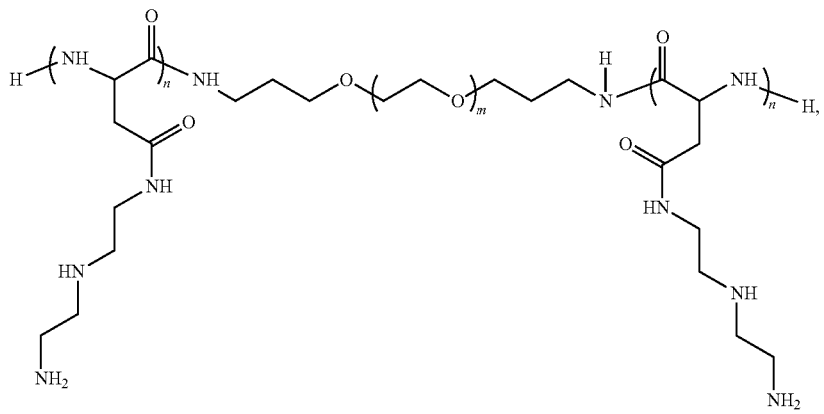

PEG-(pASP-DET)$_2$ or a salt thereof (m is the number of ethylene oxide groups in the PEG polymer, and n is the number of aspartic acid groups).

In some examples, the mRNA-polymer complex includes Formula (I):

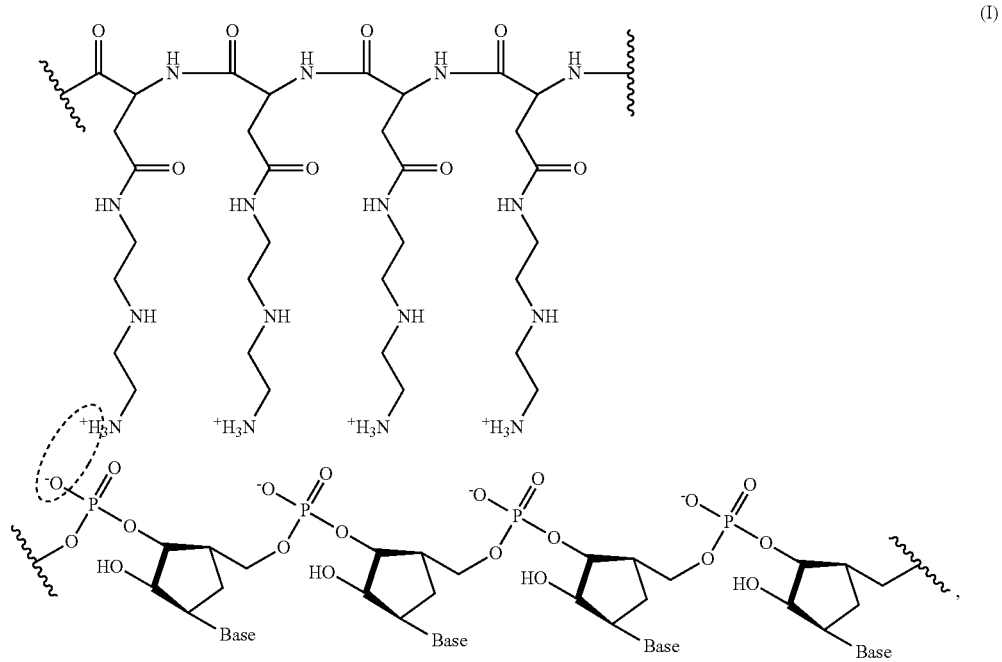

(I)

or a salt thereof, wherein the mRNA encodes a follistatin protein.

In some examples, the polymer of the complex includes an aspartic acid DET polymer, for example, an n-butyl poly{N—[N-(2-aminoethyl)aminoethyl]glutamide} cationic polymer. In some examples, the polymer of the complex includes a poly{N—[N-(2-aminoethyl)aminoethyl]glutamide} (pGLU-DET) comprising poly(glutamide) (pGLU) derivatives bearing diethylenetriamine (DET) side chains.

In some examples, the complex includes the following formula:

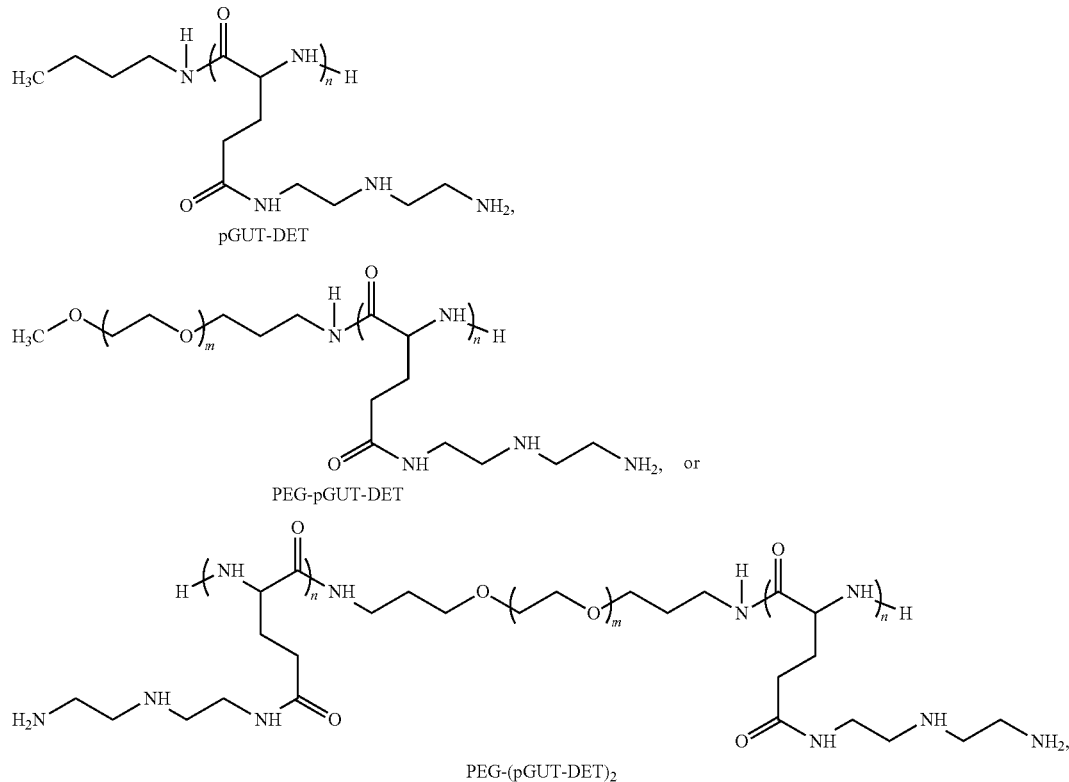

or a salt thereof (m is the number of ethylene oxide groups in the PEG polymer, and n is the number of glutamic acid groups).

In some examples, the complex includes Formula II:

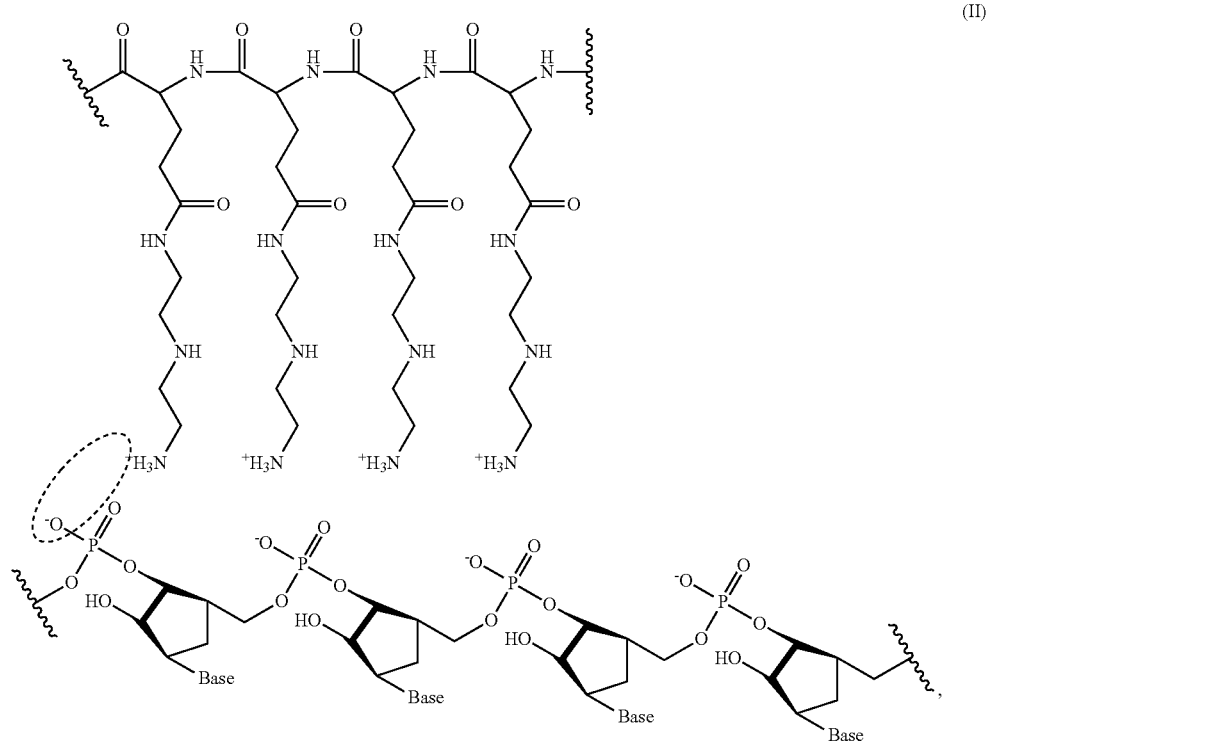

wherein the polymer is electrostatically complexed to an mRNA molecule, or a salt thereof. In some examples, the mRNA encodes a follistatin protein.

In some examples, the complex is configured for a desired level of mRNA loading and complexation of the polymer and mRNA. In specific examples, the number of polymer nitrogens and number of mRNA phosphates provide an N/P ratio of about 4. In some examples, the polymer of the complex comprises NHS-activated 5 kDa polyethylene glycol (PEG) molecules. In specific examples, the polymer further comprises a second block polyethylene glycol (PEG) molecules, with 2, 5, or 12 kDa. In some examples, the complex is configured for delivery to or uptake by hepatic cells.

Disclosed herein is a drug delivery system. In some examples, the drug delivery system includes a cationic polymer electrostatically complexed to an mRNA molecule. In specific examples, the cationic polymer of the drug delivery system is an aspartic acid polymer. In specific examples, the cationic polymer is poly[N—[N-(2-aminoethyl)-2 aminoethyl]aspartamide].

In some examples, the drug delivery system includes the following formula:

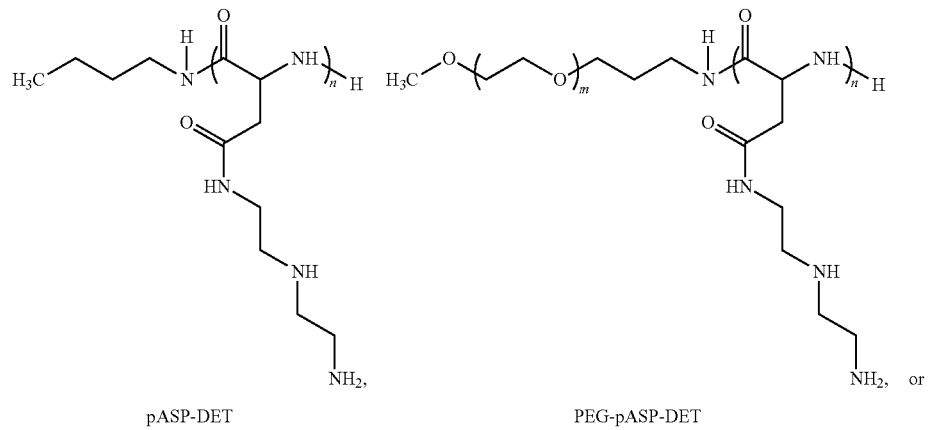

pASP-DET          PEG-pASP-DET

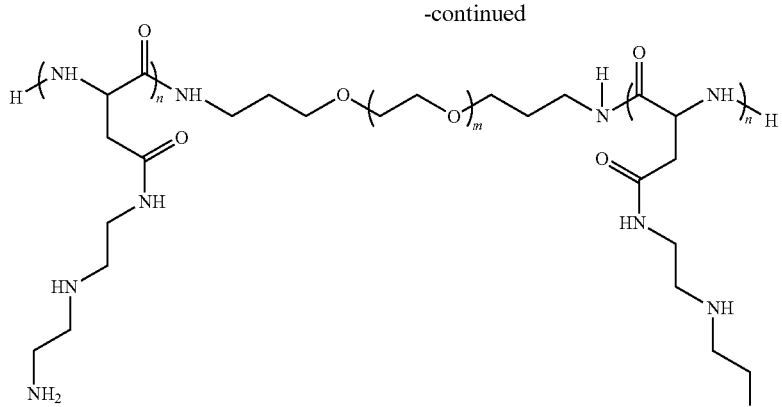

PEG-(pASP-DET)$_2$ or a salt thereof (m is the number of ethylene oxide groups in the PEG polymer, and n is the number of aspartic acid groups).

In some examples, the drug delivery system includes Formula (III):

(III)

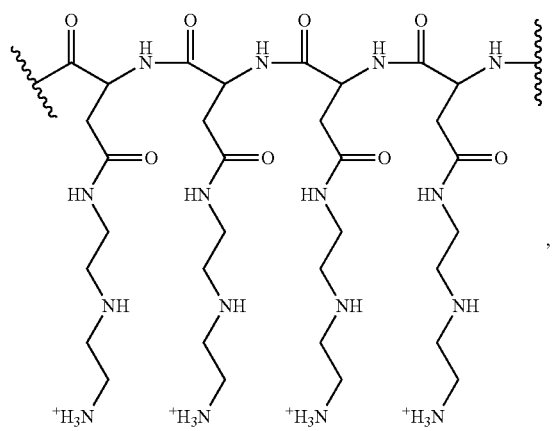

wherein the polymer is capable of electrostatic complexation with an mRNA molecule.

In some examples, the polymer of the drug delivery system is an n-butyl poly{N—[N-(2 aminoethyl)aminoethyl]glutamide} cationic polymer. In specific examples, the polymer is a poly{N—[N-(2-aminoethyl)aminoethyl] glutamide} (pGLU-DET) comprising poly(glutamide) (pGLU) derivatives bearing diethylenetriamine (DET) side chains.

In some examples, the cationic polymer of the drug delivery system includes the following formula:

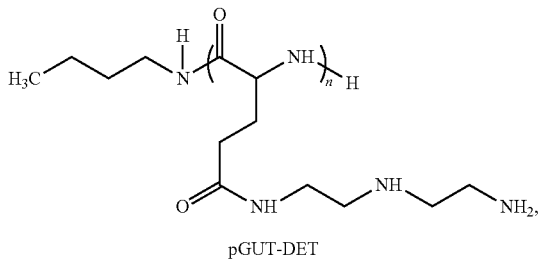

pGUT-DET

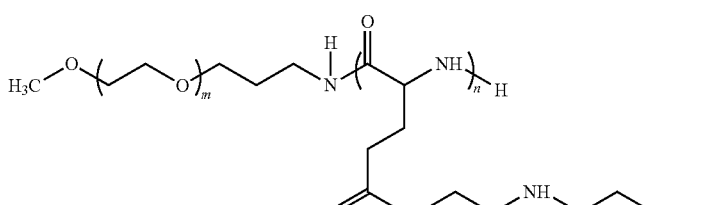

PEG-pGUT-DET

-continued

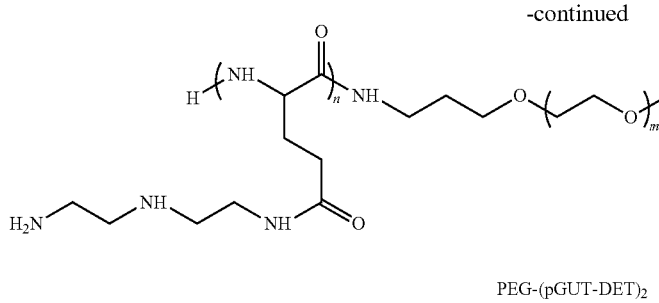
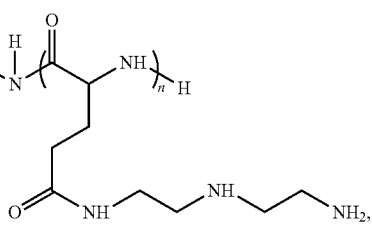

PEG-(pGUT-DET)₂ or a salt thereof (m is the number of ethylene oxide groups in the PEG polymer, and n is the number of glutamic acid groups).

In some examples, the drug delivery system includes Formula (IV):

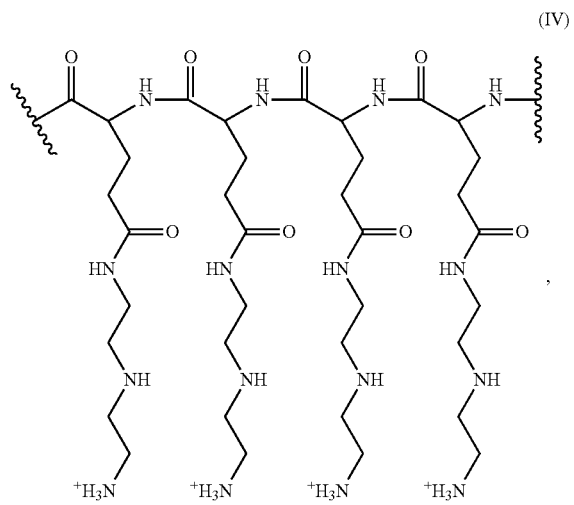 [SMILES: *NC(CCC(=O)NCCNCC[NH3+])C(=O)NC(CCC(=O)NCCNCC[NH3+])C(=O)NC(CCC(=O)NCCNCC[NH3+])C(=O)NC(CCC(=O)NCCNCC[NH3+])C(*)=O]

(IV)

wherein the polymer is capable of electrostatic complexation with an mRNA molecule.

In specific examples, the mRNA of the drug delivery system is a follistatin mRNA. In some examples, the mRNA of the drug delivery system encodes a follistatin protein with the amino acid sequence set forth in SEQ ID NO: 1, SEQ ID NO: 2, SEQ ID NO: 3, or SEQ ID NO: 4 and/or includes the nucleotide sequence set forth in SEQ ID NO: 5, SEQ ID NO: 6, SEQ ID NO: 7, or SEQ ID NO: 8.

In some examples, the drug delivery system is configured for a desired level of mRNA loading and complexation of the polymer and mRNA. In specific examples, the number of polymer nitrogens and number of mRNA phosphates in the drug delivery system provide an N/P ratio of about 4. In some examples, the drug delivery system includes NHS-activated 5 kDa polyethylene glycol (PEG) molecules. In some examples, the polymer of the drug delivery system further includes a second block polyethylene glycol (PEG) molecules with 2, 5, or 12 kDa. In some examples, the drug delivery system is configured for delivery to or uptake by hepatic cells.

Disclosed herein are methods of slowing the loss of, increasing, and/or maintaining lean muscle mass in a subject (e.g., a human and/or mammal). In some examples, the methods include administering to a subject an effective amount of an mRNA polymer complex of Formula (I) or (II). In some examples, the methods include administering to a subject an effective amount of an mRNA polymer complex of Formula (I) or (II). In some examples, the methods can include administering to a subject an effective amount (e.g., a therapeutically effective amount) of the mRNA polymer complex of Formula (I) or (II) or the drug delivery system of Formula (III) or (IV).

In specific examples, the methods can include administering the complex or system every 3 days. In specific examples, the methods can include administering the complex or system subcutaneously. In specific examples, the methods can include assessing toxicity and/or inflammation after administration.

In some examples, the methods can include selecting a subject in need of augmented muscle growth. In specific examples, the methods can include selecting a subject that has acute or chronic muscle atrophy and/or a muscle-wasting disease, wherein administering the complex treats the muscle atrophy and/or a muscle-wasting disease. In specific examples, the subject can have sarcopenia, cachexia, cancer, congestive heart failure, renal failure, chronic obstructive pulmonary disease, severe burns, an inflammatory muscle disease, myasthenia gravis, neuropathy, polio, multiple sclerosis, anorexia nervosa, human immunodeficiency virus, acquired immune deficiency syndrome, osteomalacia, herniated disk, hypercalicemia, kwashiorkor, Creutzfeldt-Jakob disease, bovine spongiform encephalopathy, diabetes, amyotrophic lateral sclerosis, necrotizing vasculitis, abetalipoproteinemia, malabsorption syndrome, legg-calve-perthes disease, muscular dystrophy, polymyositis, Guillain-Barre syndrome, and/or osteoarthritis and/or have been exposed to a zero-gravity environment.

In some examples, the complex or system is non-toxic, biocompatible with the subject, non-inflammatory, and/or eliminated from the subject with a half-life of 60-84 hours. In some examples, administration of the complex or system increases follistatin levels, decreases myostatin levels, and/or decreases activin A levels. In some examples, administration of the complex or system does not produce side effects in the subject. In specific examples, administration of the complex or system produces a therapeutic response for at least 3 days. In specific examples, administration of the complex or system lowers body fat in the subject by at least 25%. In specific examples, administration of the complex or system increases muscle mass in the subject by at least 10%.

The foregoing and other features of the disclosure will become more apparent from the following detailed description, which proceeds with reference to the accompanying figures.

BRIEF DESCRIPTION OF THE DRAWINGS

FIG. 4C shows viability of Huh 7 human liver cells treated for 48 h with non- and PEG-modified mRNA nanoparticles prepared at the following N/P ratios: 0.5, 1, 2, 4, and 8. FIGS. 4D and 4E show representative fluorescence microscopy images of Huh 7 cells incubated for 48 h with the nanoparticles loaded with the Cy5-labeled mRNA encoding for green fluorescent protein (GFP). Images represent fluorescence signal from Cy5-labeled mRNA (FIG. 4D) and fluorescence signal generated by the expressed GFP (FIG. 4E). FIG. 4F shows follistatin concentrations in the cell culture media quantified with the ELISA assay after incubation of Huh7 and HEK 293 human kidney cells for 48 h with and without nanoparticles containing FS-344 mRNA (250 ng/mL and 500 ng/mL).

FIG. 6A shows follistatin serum levels at various time points after a single SubQ injection of the nanoparticles containing FS-344 mRNA (0.5 mg/kg). FIG. 6B shows follistatin serum levels 24 h after the 1st and 16th injections. Mice were injected every 72 h for eight weeks with the nanoparticles (treatment) or saline (control). Serum concentrations of follistatin were analyzed with the ELISA assay. *$p<0.05$ when compared with a protein level in serum of non-treated animals.

FIG. 7A shows blood levels of alkaline phosphatase (ALP), alanine aminotransferase (ALT), aspartate aminotransferase (AST), and gamma-glutamyl transferase (GGT), demonstrating liver function, as well as creatine kinase (CK) blood levels, demonstrating heart and skeletal muscle function, and FIG. 7B shows blood levels of blood urea nitrogen (BUN), demonstrating kidney function. FIG. 7C shows expression of inflammatory genes in the livers of non-treated mice (control) and mice injected every 72 h for 8 weeks with the FS-344 mRNA loaded nanoparticles (0.5 mg/kg).

FIGS. 8A-8B show the percent change in lean muscle mass (FIG. 8A) and fat mass (FIG. 8B) of the baseline in non-treated mice (control) and mice treated with the FS-344 mRNA-loaded nanoparticles (0.5 mg/kg). Wild type 17-week-old C57BL/6L mice were SubQ injected with either saline (control) or the nanoparticles every three days during 8 weeks. The lean and fat mass values obtained prior to treatment were used as baseline for subsequent analyses. The average baseline values were not significantly different among the treatment and control groups. *$p<0.05$ when compared with non-treated animals. FIG. 8C shows the average weights of gastrocnemius and triceps muscles resected from non-treated and treated mice. *$p<0.05$ when compared with tissue weights resected from non-treated mice. FIG. 8D shows photographs of hind legs muscles of non-treated and treated mice.

FIG. 9C shows the average weights of hearts, kidneys, spleens, and livers resected from non-treated and treated mice. *$P<0.05$ when compared with tissue weights resected from non-treated mice.

FIGS. 13B-13C) in non-treated mice (0 h) and mice SubQ injected with the FS-344 mRNA-loaded nanoparticles (0.5 mg/kg).

SEQUENCE LISTING

Figure 1:
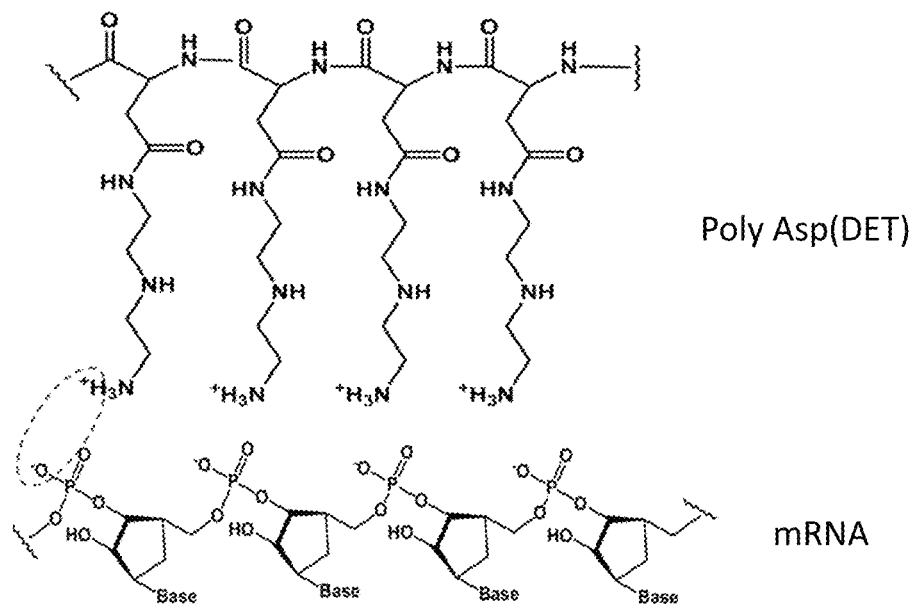
FIG. 1 shows a segment of a cationic aspartic acid DET polymer electrostatically complexed with an mRNA molecule.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Apr. 26, 2018, 5 KB, which is incorporated by reference herein. In the accompanying sequence listing:

SEQ ID NOs: 1-4 are exemplary follistatin protein sequences.

SEQ ID NOs: 5-8 are exemplary follistatin nucleic acid sequences.

Abbreviations pGUT-DET: N-butylamine-poly{N—[N-(2-aminoethyl)aminoethyl]glutamide}

PEG-pGUT-DET: Polyethylene glycol-b-poly{N—[N-(2-aminoethyl)aminoethyl]glutamide}

PEG-(pGUT-DET)$_2$: Polyethylene glycol-b-[poly{N—[N-(2-aminoethyl)aminoethyl]glutamide}]$_2$ pASP-DET: N-butylamine-poly{N—[N-(2-aminoethyl)aminoethyl]aspartamide}

PEG-pASP-DET: Polyethylene glycol-b-poly{N—[N-(2-aminoethyl)aminoethyl]aspartamide}

PEG-(pASP-DET)$_2$: Polyethylene glycol-b-[poly{N—[N-(2-aminoethyl)aminoethyl]aspartamide}]$_2$

DETAILED DESCRIPTION

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Dates of GENBANK® Accession Nos. referred to herein are the sequences available at least as early as Apr. 26, 2018. All references and GENBANK® Accession numbers cited herein are incorporated by reference in their entirety.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

In order to facilitate review of the various embodiments of the disclosure, the following explanations of specific terms are provided.

Activin A: Also known as activing β A, activin A is well-known for stimulating FSH secretion and regulating the menstrual cycle, but activin A also plays a role in reducing muscle mass. It was reported that circulating activin A levels are elevated in humans with cancer cachexia, and are directly proportional to the degree of muscle wasting (Loumaye et al., The Journal of clinical endocrinology and metabolism, 100:2030-2038, 2015; Togashi et al., Cancer Lett, 356:819-827, 2015; https://clinicaltrials.gov/ct2/show/NCT03162042 ClinicalTrials.gov Identifier: NCT03162042, 2017). Recent preclinical studies suggested that production of activin A by cancer tumors contribute to cachexia (https://clinicaltrials.gov/ct2/show/NCT03162042 ClinicalTrials.gov Identifier: NCT03162042, 2017; Zhou et al., Cell, 142:531-543, 2010) and its blockade by a soluble form of the ActRIIB receptor prevents muscle atrophy in mice.

Includes activin A nucleic acid molecules and proteins. Activin A sequences are publicly available. For example, GenBank® Accession Nos. D49743.1, AF045163.1, and D83214.2 disclose exemplary human, rat, and mouse activin A nucleotide sequences, respectively, and GenBank® Accession Nos. CAA40805.1 and P08476.2 disclose exemplary human and rat activin A protein sequences, respectively, all of which are incorporated herein by reference. One of ordinary skill in the art can identify additional activin A nucleic acid and protein sequences, including activin A variants that retain activin A biological activity (such as reducing muscle mass).

Administration/delivery: To provide or give a subject an agent (e.g., an mRNA polymer complex or a drug delivery system disclosed herein) by any effective route (e.g., any systemic or local route). Exemplary routes of administration include injection and/or infusion (e.g., subcutaneous, intravenous, intra-arterial, and/or intramuscular). Administration includes one or more doses over a short or long period of time as well as sustained release. In specific examples, administration includes providing at least one dose periodically (e.g., at least about every 1, 2, 3, 4, 5, 6, 7, 8, 9, or 10 days or about every 3 days, such as by injection or infusion, for example, subcutaneous injection).

Biocompatible: Biocompatibility generally refers to an agent or material (e.g., an mRNA polymer complex or a drug delivery system) that exhibits efficacy but remains non-toxic and non-inflammatory (or non-immunomodulatory) with no side effects.

Half-life: The half-life of a substance (e.g., a drug) is a measure of the decay time for discrete molecules or of the decay time for activity of a substance. The half-life is the time required for half of a given amount of molecules to decay, for a substance to lose half of its activity, or for the concentration of a substance to reach half of its steady-state value. In some examples, the half-life of a substance is the time required for the concentration of a substance in the body to decrease by 50% of the initial concentration. Drug half-lives can vary from seconds to months. In order to maintain steady state concentrations of a drug in the body, drugs are typically administered every half-life (e.g., administration of a drug every 72 hours can maintain steady state levels of a drug with a 72-hour half-life). Where the drug half-life is short (e.g., seconds to hours long), the drug must be administered multiple times per day to maintain steady state levels, but a drug with a longer half-life can be administered with less frequency. However, drugs with a much longer half-life (e.g., a months-long half-life) are generally administered with much lower frequency in order to avoid excessive accumulation.

Follistatin (FST): Also known as activing-binding protein and FSH-suppressing protein (e.g., OMIM 136470), follistatin is an autocrine glycoprotein and is expressed in most types of tissue. Follistatin can bind and neutralize TGF-β superfamily proteins, including activin and myostatin. Follistatin can include any of the follistatin isoforms, such as isoforms generated by alternative splicing and/or post-translational modifications, including FS-288, FS-300 or FS-303, FS-315, and FS-344 (see, e.g., Thompson et al., Dev Cell., 9(4):535-43, 2005, incorporated herein by reference).

Includes FST nucleic acid molecules and proteins. FST sequences are publicly available. For example, GenBank® Accession Nos. BC004107.2, NM_012561.2, and Z29532.1 disclose exemplary human, rat, and mouse FST nucleotide sequences, respectively, and GenBank® Accession Nos. AAH04107.1, AAB60704.1, and NP_001288302.1 disclose exemplary human, rat, and mouse FST protein sequences, respectively, all of which are incorporated herein by reference. One of ordinary skill in the art can identify additional FST nucleic acid and protein sequences, including FST variants that retain FST biological activity (such as producing increased muscle mass).

Inflammation: A biological response to harmful stimuli, which is particular for the stimuli. Inflammation can be acute or chronic. Acute inflammation is the initial response to the stimuli, including increased movement of plasma and leukocytes (especially granulocytes) from the blood to injured tissues. Chronic inflammation (prolonged inflammation) is a progressive shift in the type of cells at the site of inflammation (such as an increase in mononuclear cells) and includes simultaneous destruction and healing of the inflamed tissue. Abnormalities in the inflammatory response can lead to disease (e.g., myopathies, cancer, and vascular and/or cardiovascular disease). Inflammation can be assessed in multiple ways (see, e.g., Cooper et al., Genome Biol., 6(1): R5, 2005; Newton and Dixit, Cold Spring Harb Perspect Biol, 4(3):pii: a006049, 2012, both of which are incorporated herein by reference, indicating various biomarkers relevant to assaying inflammation). In some examples, inflammation can be assessed by measuring levels of expression of tumor necrosis factor (TNF), interleukin (IL)-6, IL-1b, C-reactive protein (CRP), and/or adenomatous polyposis coli (APC) genes compared with a control subject (e.g., a subject without inflammation). An agent (e.g., a disclosed mRNA polymer complex or drug delivery system) is considered non-inflammatory or non-immunomodulatory if the inflammation assay is negative.

Muscle atrophy: A decrease in muscle mass, including partial or complete muscle wasting. Atrophy can occur as a result of restricted movement as well as a zero-gravity (g) environment and occurs as a comorbidity with multiple diseases, including sarcopenia, cachexia, cancer, congestive heart failure, renal failure, chronic obstructive pulmonary disease, severe burns, an inflammatory muscle disease, myasthenia gravis, neuropathy, polio, multiple sclerosis, anorexia nervosa, human immunodeficiency virus, acquired immune deficiency syndrome, osteomalacia, herniated disk, hypercalicemia, kwashiorkor, Creutzfeldt-Jakob disease, bovine spongiform encephalopathy, diabetes, amyotrophic lateral sclerosis, necrotizing vasculitis, abetalipoproteinemia, malabsorption syndrome, legg-calve-perthes disease, muscular dystrophy, polymyositis, Guillain-Barre syndrome, and/or osteoarthritis.

Myostatin (MSTN): Also known as growth differentiation factor 8 (GDF8; e.g., OMIM 601788), myostatin is a myokine (e.g., a protein that inhibits myogenesis, or muscle cell growth and differentiation) and is a member of the transforming growth factor beta (TGF-β) family that is primarily expressed and secreted by skeletal muscle (McPherron et al, Nature, 387:83-90, 1997). Blocking or eliminating myostatin in vivo yields a significant increase in muscle mass. Circulating or intramuscular myostatin levels are elevated in many pathological wasting states (Costelli et al., Eur J Clin Invest, 38:531-538, 2008; Gonzalez-Cadavid et al., Proc Natl Acad Sci USA, 95:14938-14943, 1998; Lenk et al., Eur J Heart Fail, 11:342-348, 2009).

Myostatin negatively regulates muscle growth by binding to the activin type IIB receptor (ActRIIB) on muscle cells (Lee et al., Proc Natl Acad Sci USA, 98:9306-9311, 2001). ActRIIB signaling increases muscle proteolysis, reduces protein synthesis, and inhibits myoblast differentiation and proliferation by altering the expression of myogenic regulatory genes (Elkina et al., J Cachexia Sarcopenia Muscle, 2:143-151, 2011) pharmacological inhibition of myostatin signaling increases lean muscle mass and strength in wild-type mice (Lee et al., Proc Natl Acad Sci USA, 102:18117-18122, 2005; Whittemore et al., Biochem Biophys Res Commun, 300:965-971, 2003). Conversely, systemic administration or overexpression of myostatin induces muscle atrophy in rats and mice (Durieux et al., Endocrinology, 148:3140-3147, 2007; Zimmers et al., Science, 296:1486-1488, 2002; Xia et al., J Endocrinol, 202:1-12, 2009; Yaden et al., The Journal of pharmacology and experimental therapeutics, 349: 355-371, 2014; Gilson et al., American journal of physiology. Endocrinology and metabolism, 297:E157-164, 2009; Latres et al., Nature communications, 8:15153, 2017).

Includes myostatin nucleic acid molecules and proteins. Myostatin sequences are publicly available. For example, GenBank® Accession Nos. AF104922.1, AF019624.1, and BC105674.1 disclose exemplary human, rat, and mouse myostatin nucleotide sequences, respectively, and GenBank® Accession Nos. ABI48514.1, AAB86691.1, and AAO46885.1 disclose exemplary human, rat, and mouse myostatin protein sequences, respectively, all of which are incorporated herein by reference. One of ordinary skill in the art can identify additional myostatin nucleic acid and protein sequences, including myostatin variants that retain myostatin biological activity (such as reducing muscle mass).

Side effects: An effect from a substance administered to a subject (e.g., a drug) that is secondary to the one intended. The effect can be adverse, benign, or therapeutic.

Subject: Human and non-human animals, including all vertebrates, such as mammals and non-mammals, such as non-human primates, mice, rabbits, sheep, dogs, cats, horses, cows, chickens, amphibians, and reptiles. In many embodiments of the described methods, the subject is a human.

Toxicity: Toxicity generally refers to an adverse effect or damage to an organism by an agent or a substance. For example, an agent or a substance can be considered toxic if it damages major organs, such as liver, kidney, and/or muscle (including heart muscle). Toxicity can be assessed in multiple ways (see, e.g., Giannini et al., CMAJ, 172(3): 367-379, 2005; Kim and Moon, Biomol Ther (Seoul), 20(3): 268-272, 2012; Campion et al., Expert Opin Drug Metab Toxicol, 9(11), doi:10.1517/17425255.2013.827170, 2013; Anadón et al., Chapter 34. Biomarkers of drug toxicity. Biomarkers in Toxicology, 593-607, 2014, all of which indicate exemplary molecules associated with toxicity and can be used for a toxicity assay, incorporated herein by reference).

Treating, Treatment, and Therapy (or therapeutic response): Any success or indicia of success in the attenuation or amelioration of an injury, pathology, or condition, including any objective or subjective parameter, such as abatement, remission, diminishing or amelioration of symptoms, making the condition more tolerable to the patient, slowing the rate of degeneration or decline, making the final point of degeneration less debilitating, or improving a subject's physical or mental well-being. The treatment may be assessed by objective or subjective parameters, including the results of a physical examination, neurological examination, or psychiatric evaluations. In some examples, therapeutic response, for example, to a disclosed mRNA polymer complex or drug delivery system, is assessed by measuring expression levels of the mRNA or related molecules (e.g., expression of follistatin mRNA can be measure by follistatin levels and/or the levels of related molecules, such as myostatin and/or activin A).

Overview

Muscle atrophy is both a disease state and an aging process condition that diminishes the quality of life and is a strong indicator of treatment outcomes. There has been a high demand for therapeutics that increase lean mass while abrogating the need for special dietary and exercise requirements that are usually unattainable in people with active muscle wasting. Therefore, in some embodiments, a nanomedicine approach capable of increasing skeletal muscle mass and restricting body fat accumulation is disclosed herein. The therapeutic modality is based on polymeric nanoparticles that deliver messenger RNA (mRNA; e.g., follistatin mRNA) after administration (e.g., subcutaneous administration). The delivered mRNA directs the body (e.g., hepatic cellular machinery) to produce the protein encoded in the delivered mRNA (e.g., follistatin protein is produced by the complexed follistatin mRNA. Disclosed herein are animal studies demonstrating that follistatin mRNA-loaded nanoparticles can enter into the systemic circulation following subcutaneous injection, accumulate (e.g., in the liver), and internalize (e.g., into hepatic cells) where the released mRNA is translated into protein. In an example, follistatin serum levels were elevated 72 h post injection, and the produced follistatin efficiently reduced activin A and myostatin serum concentrations. After eight weeks of repeated injections, the lean mass content of the mice in the treatment group was ~10% higher compared with the controls. Body composition analysis further showed 28.6% lower body fat in the nanoparticle-treated mice compared with the non-treated controls. Thus, the polymeric nanoparticle mRNA delivery system disclosed herein is a novel development in mRNA technologies and the treatment of disease (e.g., of muscle atrophy and/or muscle-wasting disorders).

mRNA, mRNA Polymer Complexes, and Drug Delivery Systems

The present disclosure provides for mRNA-based therapeutic platforms and methods capable of safely and efficiently delivering an mRNA molecule to a cell as well as useful in mRNA delivery and therapeutic applications. In some examples, the mRNA molecule is translated by the cell to provide a desired protein upon delivery to a cell. In embodiments, the protein is a therapeutic protein or a protein that provides a desired change in the physiology or anatomy of a human or animal subject. For example, the mRNA molecule may encode a protein that enhances lean muscle mass or some other desirable trait (e.g., follistatin protein). In embodiments, enhancing lean muscle mass in a subject may accomplish a therapeutic purpose, augment the lean muscle mass of a healthy subject, or both.

mRNA polymer complexes and drug delivery systems are disclosed herein that can include a cationic polymer electrostatically complexed to an mRNA molecule that encodes a desired protein. The mRNA can be any mRNA molecule of interest (e.g., an mRNA that encodes a therapeutic protein or a protein that provides a desired change in the physiology or anatomy of a human or animal subject).

In some examples, the mRNA molecule encodes a follistatin protein. Any mRNA that encodes a follistatin protein can be used. Exemplary human, rat, and mouse follistatin nucleotide sequences are disclosed in GenBank® Accession Nos. BC004107.2, NM_012561.2, and Z29532.1, respectively, and exemplary human, rat, and mouse follistatin protein sequences are disclosed in GenBank® Accession Nos. AAH04107.1, AAB60704.1, and NP_001288302.1, respectively, all of which are incorporated herein by reference. In some examples, the mRNA molecule encodes a follistatin protein having the amino acid sequence set forth in SEQ ID NO: (also referred to herein as FS-344; e.g., GenBank® Accession No. AAH04107.1) or SEQ ID NO: 2 (also referred to herein as FS-315 or an FS-344 splicing product; e.g., GenBank® Accession No. 2P6A_C, incorporated herein by reference). In some examples, the mRNA molecule encodes a follistatin protein having the amino acid sequence set forth in SEQ ID NO: 3 (also referred to herein as FS-317; e.g., GenBank® Accession No. NP_006341.1) or SEQ ID NO: 4 (also referred to herein as FS-288 or an FS-317 splicing product; e.g., GenBank® Accession No. 3HH2_D). In some examples, the mRNA molecule encoding a follistatin protein can include the nucleic acid sequence set forth in SEQ ID NO: 5 (also referred to herein as FS-344 or an FS-315 precursor; e.g., GenBank® Accession No. HB426387.1) or SEQ ID NO: 6 (also referred to herein as FS-315 or an FS-344 splicing product; e.g., US Pat. Pub. No. 2016/0256526, incorporated herein by reference). In some examples, the mRNA molecule encoding a follistatin protein can include the nucleic acid sequence set forth in SEQ ID NO: 7 (also referred to herein as FS-317 or an FS-288 precursor; e.g., US Pat. Pub. No. 2015/0086636, incorporated herein by reference) or SEQ ID NO: 8 (also referred to herein as FS-288 or an FS-317 splicing product; e.g., US Pat. Pub. No. 2016/0256526, incorporated herein by reference).

In some embodiments, the mRNA molecule may include any nucleic acid sequence that encodes for the amino acid sequence set forth in SEQ ID NO: 1, SEQ ID NO: 2, SEQ ID NO: 3, and/or SEQ ID NO: 4. In some embodiments, variants of follistatin can be encoded by the mRNA molecules, such as proteins about 95%, 96%, 97%, 98%, or 99% identical to human, rat, or mouse follistatin. In some embodiments, the mRNA encodes a follistatin protein at least 95% identical to SEQ ID NO: 1, SEQ ID NO: 2, SEQ ID NO: 3, and/or SEQ ID NO: 4, such as at least 95%, at least 96%, at least 97%, at least 98%, at least 99%, or 100% identical to the amino acid sequence of SEQ ID NO: 1, SEQ ID NO: 2, SEQ ID NO: 3, and/or SEQ ID NO: 4, respectively. In further embodiments, the follistatin protein administered includes at most 1, 2, 3, 4, 5, 6, 7, 8, 9, or 10 conservative substitutions in SEQ ID NO: 1, SEQ ID NO: 2, SEQ ID NO: 3, and/or SEQ ID NO: 4, wherein the protein retains at least one biological activity of follistatin, such as producing increased muscle mass. In yet other embodiments, the mRNA encoding follistatin is at least 85% identical to SEQ ID NO: 5, SEQ ID NO: 6, SEQ ID NO: 7, and/or SEQ ID NO: 8, for example, a nucleic acid molecule that is at least 85%, at least 90%, at least 95%, at least 96%, at least 97%, at least 98%, at least 99%, or 100% identical to SEQ ID NO: 5, SEQ ID NO: 6, SEQ ID NO: 7, and/or SEQ ID NO: 8, respectively.

One of skill will realize that conservative variants of the proteins can be produced. Such conservative variants employed in proteins, such as follistatin proteins will retain critical amino acid residues necessary for correct folding and one or more follistatin activities (e.g., producing increase muscle mass). Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Nucleic acid molecules encoding a follistatin protein or variant thereof can be produced. Nucleic acid sequences encoding follistatin can be prepared by any suitable method including, for example, cloning or synthesis (see, e.g., Nagata et al., Nucleic Acids Res., 38(21): 7845-7857, 2010; Narang et al., Meth. Enzymol. 68:90-99, 1979; Brown et al., Meth. Enzymol. 68:109-151, 1979; Beaucage et al., Tetra. Lett. 22:1859-1862, 1981; the solid phase phosphoramidite triester Beaucage & Caruthers, Tetra. Letts. 22(20):1859-1862, 1981; Needham-VanDevanter et al., Nucl. Acids Res.

12:6159-6168, 1984; and U.S. Pat. No. 4,458,066, all of which are incorporated herein by reference). In some examples, these nucleic acids can be produced using the amino acid sequences provided herein (such as the follistatin sequences). One of skill in the art can readily use the genetic code to construct a variety of functionally equivalent nucleic acids, such as nucleic acids which differ in sequence but which encode the same follistatin protein sequence.

In embodiments, the polymer can be a polyamino acid cationic polymer. Any polyamino acid cationic polymer can be used (e.g., a polyaspartic acid or polyglutamic acid cationic polymer, such as N-substituted polyaspartamide or N-substituted polyglutamide). In some non-limiting examples, the polymer can be an aspartic acid (e.g., n-butyl polyaspartic acid) cationic polymer with a side chain substitution that includes N-(2-aminoethyl)-2-aminoethyl (DET), such as n-butyl poly{N—[N-(2-aminoethyl)aminoethyl]aspartamide}. In embodiments, the polymer contains at least about 60, 65, 70, 75, 80, 85, 90, 95, 100, 105, or 110 or about 60-110, 70-100, 70-85, 80-95, 60-65, 65-70, 70-75, 75-80, 80-85, 85-90, 90-95, 95-100, 100-105, or 105-110 or about 80 or 85 repeating aspartic acid units.

In embodiments, the cationic polymer can include the following formula:

In embodiments, the number of polymer units, represented by "n," is at least about 60, 65, 70, 75, 80, 85, 90, 95, 100, 105, 110, 115, 120, 125, 130, 135, 140, 145, 150, 155, 160, 165, 170, or 175 or about 60-175, 75-150, 80-120, 70-85, 80-95, 60-65, 65-70, 70-75, 75-80, 80-85, 85-90, 90-95, 95-100, 100-105, or 105-110 or about 80 or 85. In embodiments, the number of ethylene oxide groups in the PEG polymer, represented by "m," is at least about 2, 4, 6, 10, 15, 20, 30, 40, 50, 60, 70, 80, 90, 100, 120, 140, 160, 180, 200, 225, 250, 275, 300, or 325 or about 2-325, 40-275, 100-300, 30-60, 100-130, 260-280, 2-4, 4-6, 6-10, 10-15, 15-20, 20-30, 30-40, 40-50, 50-60, 60-70, 70-80, 80-90, 90-100, 100-120, 120-140, 140-160, 160-180, 180-200, 200-225, 225-250, 250-275, 275-300, or 300-325 or about 45, 114, or 273. In embodiments, the number of polymer units is suitable to achieve a desired level of mRNA loading or complexation.

In embodiments, the polymer is electrostatically complexed to an mRNA molecule, as represented in FIG. 1 and Formula (I):

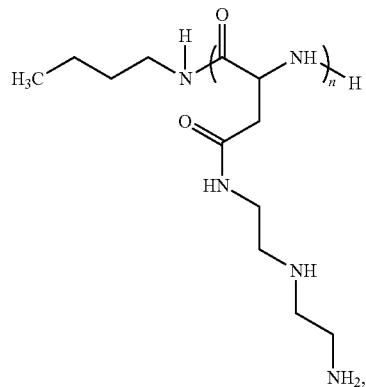

pASP-DET

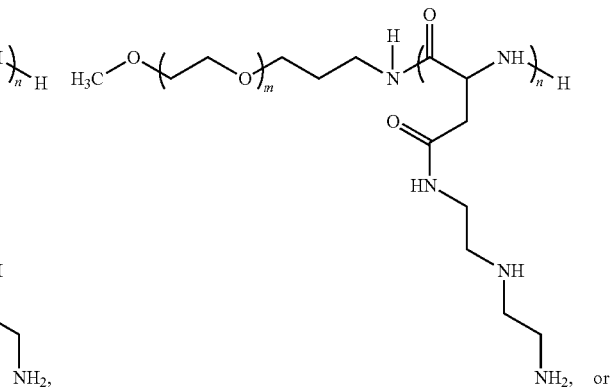

PEG-pASP-DET

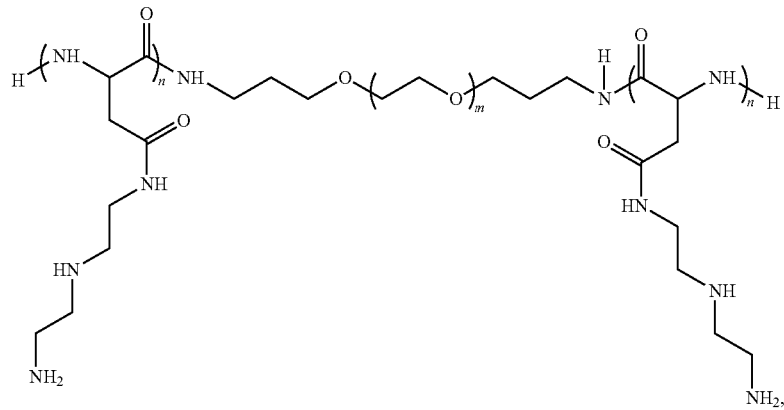

PEG-(pASP-DET)₂ or a salt thereof.

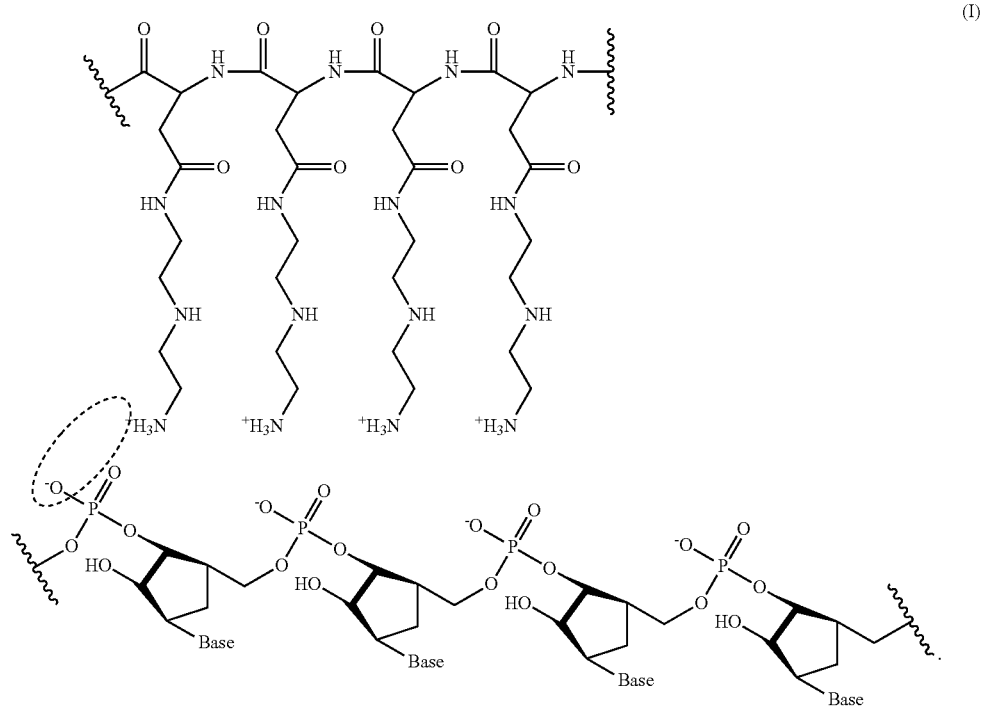

(I)

Formula I shows electrostatic complexation as a dashed circle. The mRNA can encode any protein of interest (e.g., a therapeutic or beneficial protein). In some examples, the mRNA encodes a follistatin protein.

In some examples, the polymer can be a glutamic acid (e.g., n-butyl polyglutamic acid) cationic polymer with a side chain substitution that includes N-(2-aminoethyl)-2-aminoethyl (DET), such as n-butyl poly{N—[N-(2-amino-ethyl)aminoethyl]glutamide}. In embodiments, the polymer contains at least about 60, 65, 70, 75, 80, 85, 90, 95, 100, 105, or 110 or about 60-110, 70-100, 70-85, 80-95, 60-65, 65-70, 70-75, 75-80, 80-85, 85-90, 90-95, 95-100, 100-105, or 105-110 or about 80 or 85 repeating glutamic acid units.

In embodiments, the cationic polymer can include the following formula:

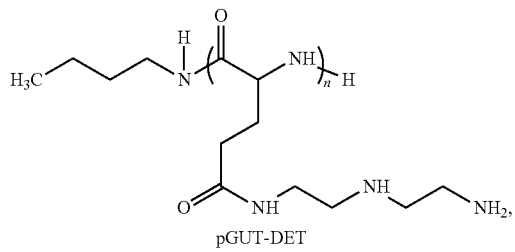

pGUT-DET

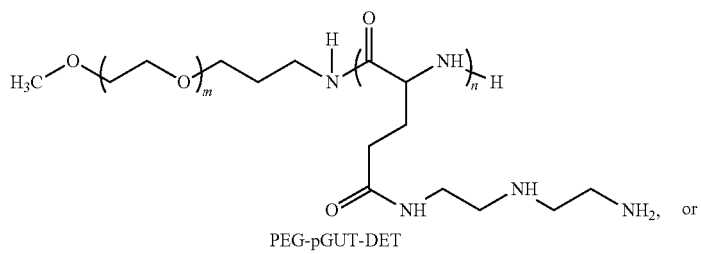

PEG-pGUT-DET

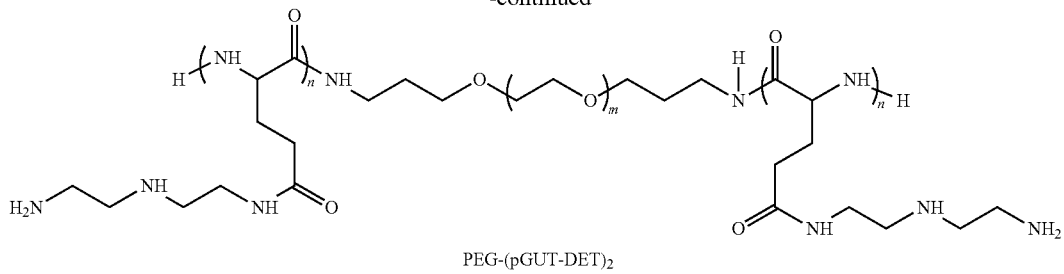

PEG-(pGUT-DET)₂ or a salt thereof.

In embodiments, the number of polymer units, represented by "n," is at least about 60, 65, 70, 75, 80, 85, 90, 95, 100, 105, 110, 115, 120, 125, 130, 135, 140, 145, 150, 155, 160, 165, 170, or 175 or about 60-175, 75-150, 80-120, 70-85, 80-95, 60-65, 65-70, 70-75, 75-80, 80-85, 85-90, 90-95, 95-100, 100-105, or 105-110 or about 80 or 85. In embodiments, the number of ethylene oxide groups in the PEG polymer, represented by "m," is at least about 2, 4, 6, 10, 15, 20, 30, 40, 50, 60, 70, 80, 90, 100, 120, 140, 160, 180, 200, 225, 250, 275, 300, or 325 or about 2-325, 40-275, 100-300, 30-60, 100-130, 260-280, 2-4, 4-6, 6-10, 10-15, 15-20, 20-30, 30-40, 40-50, 50-60, 60-70, 70-80, 80-90, 90-100, 100-120, 120-140, 140-160, 160-180, 180-200, 200-225, 225-250, 250-275, 275-300, or 300-325 or about 45, 114, or 273. In embodiments, the number of polymer units is suitable to achieve a desired level of mRNA loading or complexation.

The mRNA polymer complexes and drug delivery systems disclosed herein can include a cationic polymer. In embodiments, the cationic polymer can also include an mRNA molecule electrostatically complexed to the polymer. In some examples, the cationic polymer is an glutamic acid polymer (e.g., an n-butyl poly{N—[N-(2-aminoethyl)aminoethyl]glutamide} cationic polymer). In specific examples, the mRNA polymer complex and/or drug delivery system includes a polymer with the following formula:

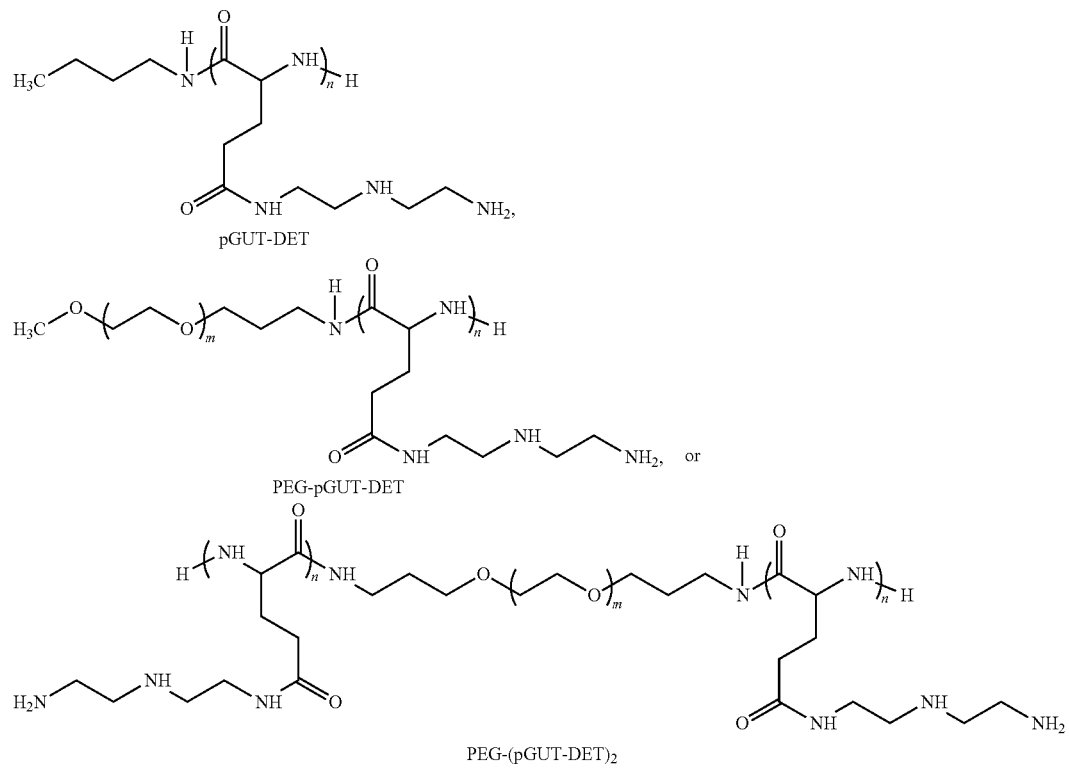

or a salt thereof (m is the number of ethylene oxide groups in the PEG polymer, and n is the number of aspartic acid groups).

Figure 2:
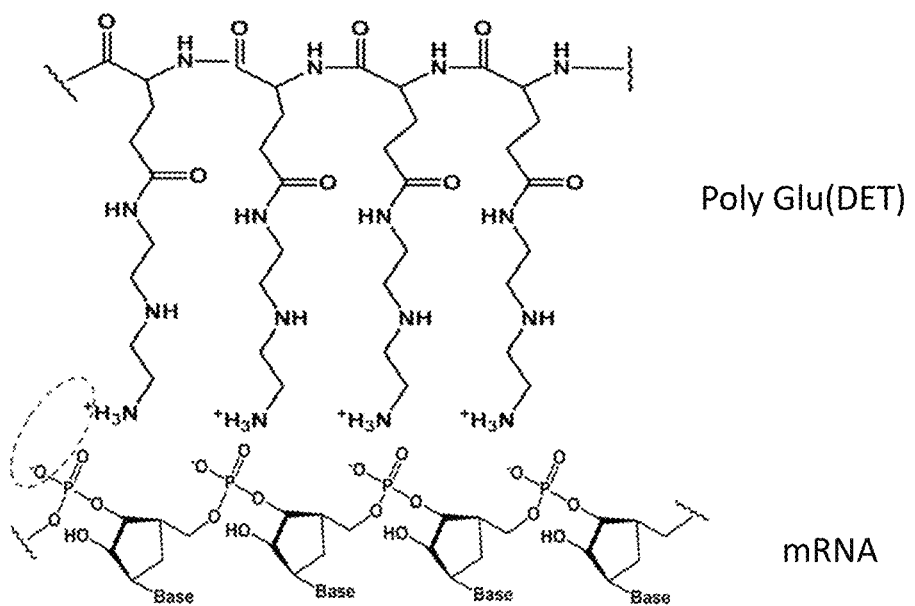
FIG. 2 shows a segment of a glutamic acid DET polymer electrostatically complexed with an mRNA molecule.

In embodiments, the polymer is electrostatically complexed to an mRNA molecule, as represented in FIG. 2 and Formula II:

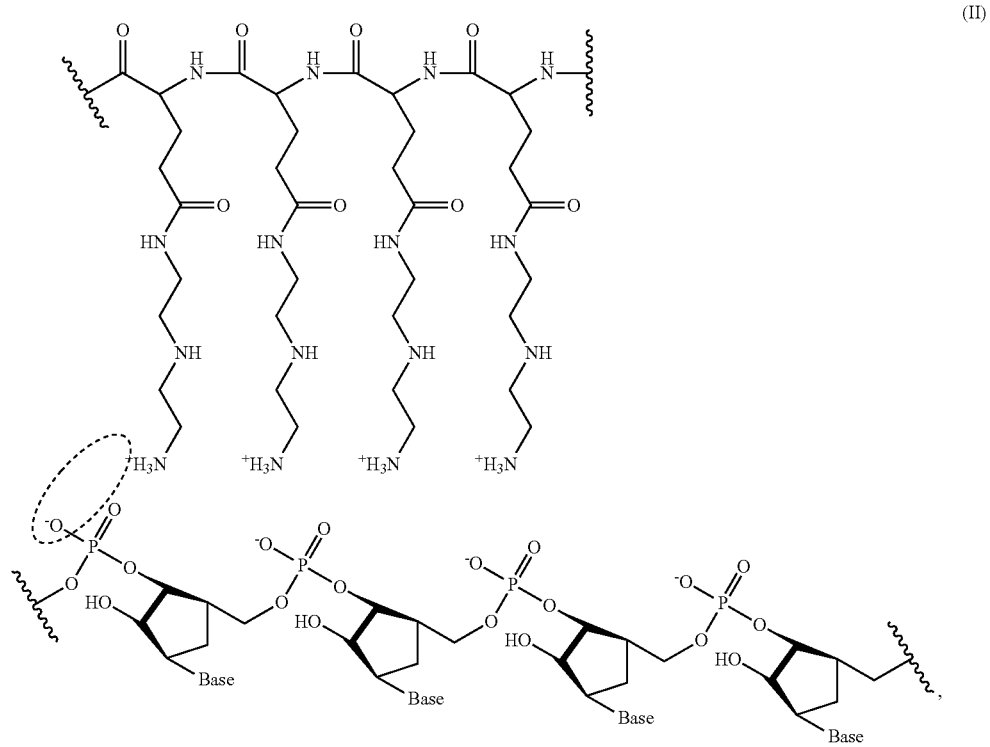

(II)

wherein the mRNA is electrostatically complexed to the mRNA molecule. In embodiments, the mRNA encodes a therapeutic or otherwise beneficial protein (e.g., follistatin protein).

In some examples, the cationic polymer is an aspartic acid polymer (e.g., an n-butyl poly{N—[N-(2-aminoethyl)aminoethyl]aspartamide} cationic polymer). In some examples, the aspartic acid polymer that includes polyaspartamide (poly(ASP)) derivatives bearing diethylenetriamine (DET) side chains (e.g., poly{N—[N-(2-aminoethyl)aminoethyl]aspartamide} pASP(DET)). In specific examples, the mRNA polymer complex and/or drug delivery system comprises a polymer comprising the following formula:

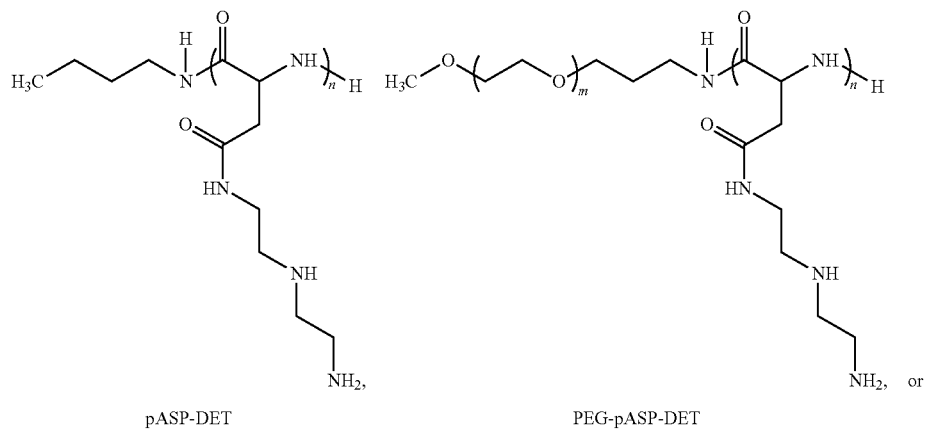

pASP-DET           PEG-pASP-DET

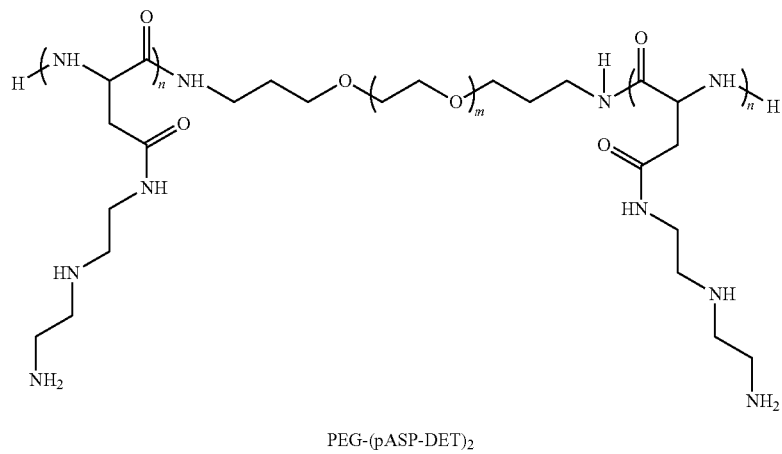

PEG-(pASP-DET)₂ or a salt thereof.

In embodiments, the number of polymer units, represented by "n," is at least about 60, 65, 70, 75, 80, 85, 90, 95, 100, 105, 110, 115, 120, 125, 130, 135, 140, 145, 150, 155, 160, 165, 170, or 175 or about 60-175, 75-150, 80-120, 70-85, 80-95, 60-65, 65-70, 70-75, 75-80, 80-85, 85-90, 90-95, 95-100, 100-105, or 105-110 or about 80 or 85. In embodiments, the number of ethylene oxide groups in the PEG polymer, represented by "m," is at least about 2, 4, 6, 10, 15, 20, 30, 40, 50, 60, 70, 80, 90, 100, 120, 140, 160, 180, 200, 225, 250, 275, 300, or 325 or about 2-325, 40-275, 100-300, 30-60, 100-130, 260-280, 2-4, 4-6, 6-10, 10-15, 15-20, 20-30, 30-40, 40-50, 50-60, 60-70, 70-80, 80-90, 90-100, 100-120, 120-140, 140-160, 160-180, 180-200, 200-225, 225-250, 250-275, 275-300, or 300-325 or about 45, 114, or 273. In embodiments, the number of polymer units is suitable to achieve a desired level of mRNA loading or complexation.

In embodiments, the cationic polymer is a polymer of Formula (III):

and is capable of electrostatic complexation with an mRNA molecule. In embodiments, the mRNA molecule includes a therapeutic or otherwise beneficial protein.

In some examples, the cationic polymer is a glutamic acid polymer (e.g., an n-butyl poly{N—[N-(2-aminoethyl)aminoethyl] glutamide} cationic polymer). In some examples, the glutamic acid polymer that includes polyglutamide (poly (GLU)) derivatives bearing diethylenetriamine (DET) side chains (e.g., poly{N—[N-(2-aminoethyl)aminoethyl]glutamide} pGLU(DET)). In specific examples, the mRNA polymer complex and/or drug delivery system comprises a polymer comprising the following formula:

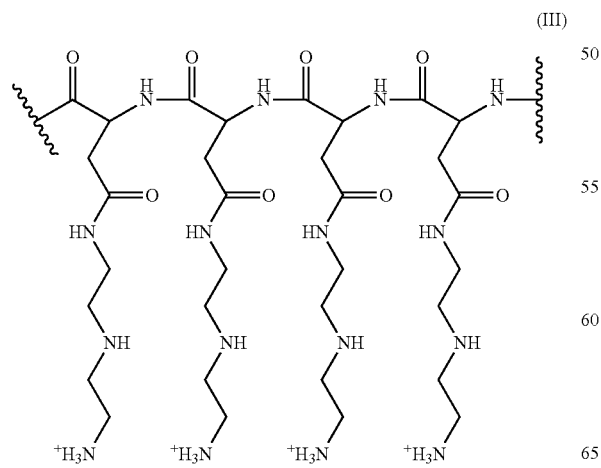

(III)

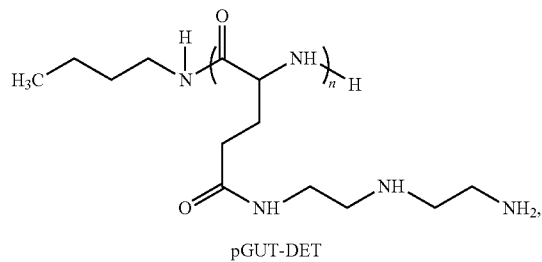

pGUT-DET

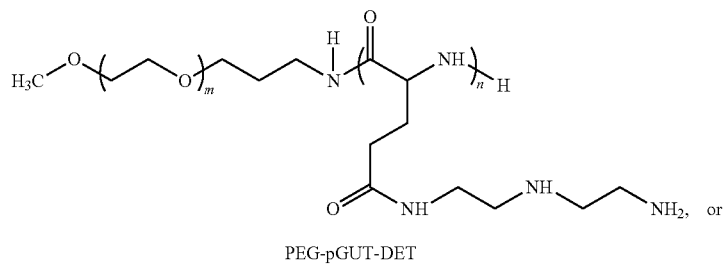

PEG-pGUT-DET

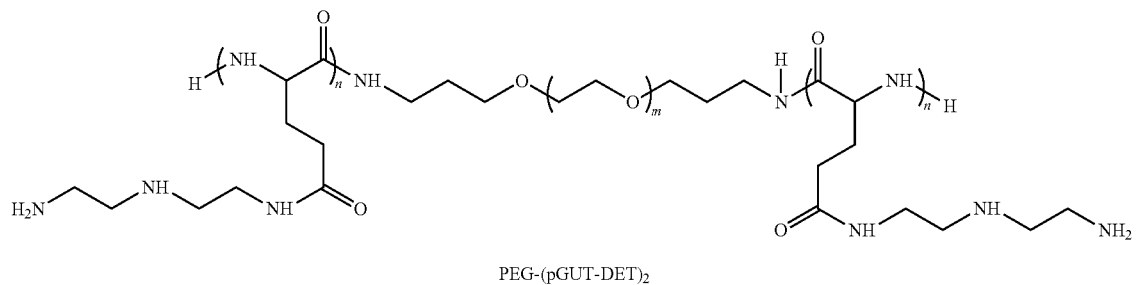

PEG-(pGUT-DET)₂ or a salt thereof.

In embodiments, the number of polymer units, represented by "n," is at least about 60, 65, 70, 75, 80, 85, 90, 95, 100, 105, 110, 115, 120, 125, 130, 135, 140, 145, 150, 155, 160, 165, 170, or 175 or about 60-175, 75-150, 80-120, 70-85, 80-95, 60-65, 65-70, 70-75, 75-80, 80-85, 85-90, 90-95, 95-100, 100-105, or 105-110 or about 80 or 85. In embodiments, the number of ethylene oxide groups in the PEG polymer, represented by "m," is at least about 2, 4, 6, 10, 15, 20, 30, 40, 50, 60, 70, 80, 90, 100, 120, 140, 160, 180, 200, 225, 250, 275, 300, or 325 or about 2-325, 40-275, 100-300, 30-60, 100-130, 260-280, 2-4, 4-6, 6-10, 10-15, 15-20, 20-30, 30-40, 40-50, 50-60, 60-70, 70-80, 80-90, 90-100, 100-120, 120-140, 140-160, 160-180, 180-200, 200-225, 225-250, 250-275, 275-300, or 300-325 or about 45, 114, or 273. In embodiments, the number of polymer units is suitable to achieve a desired level of mRNA loading or complexation.

In embodiments, the polymer comprises Formula (IV):

(IV)

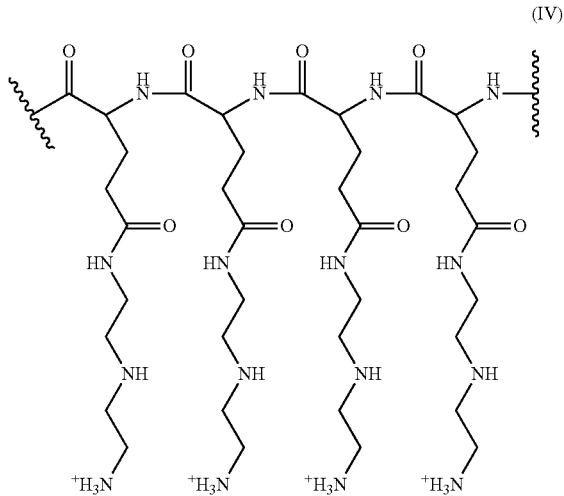 [SMILES: *NC(CCC(=O)NCCNCC[NH3+])C(=O)NC(CCC(=O)NCCNCC[NH3+])C(=O)NC(CCC(=O)NCCNCC[NH3+])C(=O)NC(CCC(=O)NCCNCC[NH3+])C(*)=O]

and is capable of electrostatic complexation with an mRNA molecule.

In embodiments, an mRNA polymer complex of the present disclosure is configured for a desired level of mRNA loading or complexation of the polymer and mRNA. In one example, a desired level of mRNA loading or complexation is achieved by manipulating the number of polymer nitrogens or the number of mRNA phosphates to provide a desired nitrogen to phosphate (N/P) ratio. In embodiments, the N/P ratio is at least about 1, 2, 3, 4, 5, 6, 7, or 8 or about 1-8, 2-5, 3-7, 4-6, 1-2, 2-3, 3-4, 4-5, 5-6, 6-7, or 7-8 or about 4, for example, at a concentration of at least about 1, 2, 5, 10, 15, 20, 30, 40, or 50 µg or about 1-50, 5-25, 10-30, 20-40, 30-50, 1-5, 5-15, 2-10, 1-2, 2-5, 5-10, 10-15, 15-20, 20-30, 30-40, or 40-50 µg or about 10 µg.

In embodiments, the polymer component of the mRNA polymer complex contains excess surface primary amines to facilitate further surface modifications. In embodiments, the polymer surface is modified to contain polyethylene glycol (PEG) molecules. Addition of PEG can improve systemic circulation time and biocompatibility of the mRNA delivery system as well as reduce toxicity. The PEG can have any molecular weight. In some examples, the PEG is at least about 0.5, 1, 2, 3, 4, 5, 6, 7, 8, 9, 10, 12, 15, 20, 30, 40, 50, 100, 200, or 500 kDa or about 0.5-1, 1-2, 2-3, 3-4, 4-5, 5-6, 6-7, 7-8, 8-9, 9-10, 10-12, 12-15, 15-20, 20-30, 30-40, 40-50, 50-100, 100-200, or 200-500 kDa or about 5 kDa. In some non-limiting examples, the PEG has a molecular weight of about 2, 5, or 12 kDa. The surface modifications (e.g., PEG) can be coupled (e.g., cross-linked) to the polymer using any method. In some examples, peptide coupling or cross-linking agents can be used, such as N-hydroxysuccinimide (NHS), sulfo-NHS, hydroxybenzotriazole (HOBt), 1-hydroxy-7-azabenzotriazole (HOAt), and/or pentafluorophenol. In specific examples, NHS can be used to couple surface modifications (e.g., PEG, such as 5 kDA PEG) to the polymer. Any number of surface modifications can be coupled to the polymer. In specific examples, a second block of PEG molecules (e.g., PEG at least about 0.5, 1, 2, 3, 4, 5, 6, 7, 8, 9, 10, 12, 15, 20, 30, 40, 50, 100, 200, or 500 kDa or about 0.5-1, 1-2, 2-3, 3-4, 4-5, 5-6, 6-7, 7-8, 8-9, 9-10, 10-12, 12-15, 15-20, 20-30, 30-40, 40-50, 50-100, 100-200, or 200-500 kDa or about 2, 5, or 12 kDa).

In some examples, the complex includes a salt of the polymer, such as a pharmaceutically acceptable salt. Such salts include those formed from cations, such as sodium, potassium, aluminum, calcium, lithium, magnesium, and zinc, and from bases, such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. Pharmaceutically acceptable salts are also inclusive of the free acid, base, and zwitterionic forms. Description of suitable pharmaceutically acceptable salts can be found in *Handbook of Pharmaceutical Salts, Properties, Selection and Use*, Wiley VCH, 2002.

In some embodiments of the invention, the mRNA may optionally have chemical or biological modifications that, for example, improve the stability and/or half-life or improve or facilitate protein production for the mRNA (see, e.g., WO 2014/152940, incorporated herein by reference). The mRNA may retain at least some ability to be translated, thereby producing a functional protein (e.g., follistatin).

Exemplary modifications include those that confer increased or enhanced stability to the nucleic acid, including, for example, improved resistance to nuclease digestion in vivo; chemical or biological modification that renders the mRNA more stable (e.g., deletion, substitution, covalent modification, and/or introduction of a nucleotide analog); and/or altered codon sequences that code for the same amino acid but render the mRNA more stable. Other modifications are possible, for example, incorporation of non-nucleotide linkages or modified nucleotides, such as addition of bases to an mRNA sequence (e.g., a poly A tail or a longer poly A tail), an altered 3' UTR or 5' UTR, additional complexation of the mRNA with an agent (e.g., a protein or a complementary nucleic acid molecule), and elements that change the structure.

In embodiments, the cationic polymer provides biodegradability, biocompatibility, or endosomal escape properties. In some embodiments, the mRNA polymer complex and/or drug delivery system is configured for delivery to or uptake by target organs and/or cells (e.g., liver and/or hepatic cells). In some examples, the mRNA polymer complex and/or drug delivery system is configured for delivery to or uptake by the liver and/or hepatic cells, such as by tuning the N/P (positive polymer amine/negative mRNA phosphate) ratio to produce a nanoparticle, for example, by spontaneous electrostatic interaction between the negatively charged phosphate groups of mRNA and positively charged primary amines of DET between two or more mRNA polymer complexes. In specific examples, the N/P ratio is at least about 1, 2, 3, 4, 5, 6, 7, or 8 or about 1-8, 2-5, 3-7, 4-6, 1-2, 2-3, 3-4, 4-5, 5-6, 6-7, or 7-8 or about 4, such as with a hydrodynamic diameter of at least about 45, 50, 60, 70, 80, 90, 100, 110, 120, or 130 nm or about 45-130, 50-110, 70-90, 45-50, 50-60, 60-70, 70-80, 80-90, 90-100, 100-110, 110-120, or 120-130 nm or about 80 nm. Without being bound by theory, such targeted delivery or uptake will result in the targeted organs or cells (e.g., liver and/or hepatic cells) acting as the primary source of protein production, which will allow for protein excretion into systemic circulation (e.g., through the hepatic portal vein).

In other embodiments, the mRNA polymer complex and/or drug delivery system shows no preference for delivery or uptake by the targeted organs and/or cells (e.g., liver and/or hepatic cells), relative to cells of other organs (e.g., other major clearance organs and/or cells, such as kidney and/or kidney cells), but the targeted organs and/or cells nonetheless provide for increased protein production (e.g., from the liver and/or hepatic cells), relative to production in other organs and/or cells (e.g., other clearance organs and/or cells). In some examples, the targeted organs are the liver and/or hepatic cells, and the mRNA polymer complex and/or drug delivery system provided for increased protein production, such as by endogenously produced and post-translationally modified by the machinery of the transfected cells during an extended period of time (see, e.g., Kaczmarek et al., Genome medicine, 9:60, 2017, incorporated herein by reference). In some embodiments, accumulation of the mRNA polymer complex and protein expression in organs other than the kidney and liver is low. For example, protein expression in other organs may be undetectable or nearly undetectable in a standard biodistribution study.

In some embodiments, the mRNA polymer complex is configured or administered to achieve a biodistribution profile that favors accumulation or expression of a therapeutic protein in the liver. For example, accumulation of produced protein starting as early as at least about 1, 2, 3, 4, 5, or 6 hours or about 1-2, 2-3, 3-4, 4-5, or 5-6 hours or about 4 hours and increases until at least about the 9, 10, 11, 12, 13, 14, 15, or 16 hour time point or about the timepoint between 9-10, 10-11, 11-12, 12-13, 13-14, 14-15, or 15-16 hours or about the 12 hour timepoint, with a timepoint approximating the maximal production time point after administration. In embodiments, protein production is maintained for at least about 12, 24, 36, 48, 60, 72, 84, 96, 108, 120, 132, 144, 156, 168, 180, or 192 hours or about 12-48, 24-72, 36-84, 60-96, 72-120, 96-144, 108-180, 132-192, 12-24, 24-36, 36-48, 48-60, 60-72, 72-84, 84-96, 96-108, 108-120, 120-132, 132-144, 144-156, 156-168, 168-180, or 180-192 or about 168 hours after a single bolus injection, which may be achieved, at least in part, by, for example, subcutaneous extended release profile of the mRNA polymer complex as well as the mRNA and protein half-lives. In embodiments, protein production in the liver is from at least about 0.1-, 0.2-, 0.3-, 0.4-, 0.5-, 0.6-, 0.7-, 0.8-, 0.9-, or 1-fold or about 0.1- to 0.2-, 0.2- to 0.3-, 0.3- to 0.4-, 0.4- to 0.5-, 0.5- to 0.6-, 0.6- to 0.7-, 0.7- to 0.8-, 0.8- to 0.9-, or 0.9- to 1-fold or about 0.21- to 0.75-fold greater than in the kidney. Protein expression may be determined using any technique (e.g., immunohistochemistry, IHC) at any desired timepoint. In embodiments, protein expression is determined at least at one or more of 12, 24, 36, 48, 60, 72, 84, 96, 108, 120, 132, 144, 156, 168, 180, and/or 192 hour timepoints and/or about 12-48, 24-72, 36-84, 60-96, 72-120, 96-144, 108-180, 132-192, 12-24, 24-36, 36-48, 48-60, 60-72, 72-84, 84-96, 96-108, 108-120, 120-132, 132-144, 144-156, 156-168, 168-180, and/or 180-192 hour timepoints and/or about 12, 24, 96, and/or 168 hour timepoints.

Pharmaceutical and Therapeutic Compositions

Pharmaceutical and/or therapeutic compositions are disclosed herein that can include an effective amount (e.g., a therapeutically effective amount) of any mRNA polymer complex or drug delivery system disclosed herein. The mRNA polymer complex or drug delivery system (e.g., as included in a pharmaceutical and/or therapeutic composition) can be formulated and administered in a variety of ways depending on the location and type of disease to be treated. In some examples, the mRNA polymer complex or the drug delivery system can be formulated for administration in human or veterinary medicine. In some examples, the mRNA polymer complex or the drug delivery system can be formulated for systemic or local use. In specific examples, the mRNA polymer complex or drug delivery system is formulated for systemic use. Actual methods of preparing or formulating such compositions or dosage forms are known or will be apparent to those of ordinary skill in the art. The amount of the mRNA polymer complex or drug delivery system administered will depend on the subject being treated, the severity of the condition being treated, and the manner of administration and is best left to the judgment of the prescribing clinician. Within these bounds, the composition or dosage form for administration will contain a quantity of the a mRNA polymer complex or drug delivery system in amounts effective to achieve the desired effect in the subject being treated (e.g., a therapeutically effective amount).

Any mRNA polymer complex or drug delivery system disclosed herein (e.g., as included in a pharmaceutical and/or therapeutic composition) can be administered through any type of route (see, e.g., Kaczmarek et al., Genome Medicine, 9:60, 2017, and Guild et al., WO 2012/170930, both of which are incorporated herein by reference). Exemplary routes include parenteral administration, such as injection or infusion (e.g., subcutaneous, intravenous, intra-arterial, or intramuscular injection or infusion). In specific examples, the mRNA polymer complex or drug delivery system is administered to the subject subcutaneously, such as through subcutaneous injection. In specific examples, subcutaneous administration is selected because 1) it elicits an extended release profile into systemic circulation with absorption rates slower than intramuscular delivery, 2) a patient can administer the therapy at home with no clinician assistance, and/or 3) it allows for sustained release formulation versatility (e.g., using hydrogel formulations).

Such compositions can be formulated generally by mixing a disclosed mRNA polymer complex or drug delivery system at the desired degree of purity in a unit dosage injectable form (e.g., a solution, suspension, or emulsion) with a pharmaceutically acceptable carrier (e.g., a carrier that is non-toxic to recipients at the dosages and concentrations employed and is compatible with other ingredients of the formulation). In addition, the mRNA polymer complexes or drug delivery systems disclosed herein can be suspended in an aqueous carrier (e.g., an isotonic or hypotonic buffer solution at a pH of about 3.0 to about 8.5, such as about 4.0 to about 8.0, about 6.5 to about 8.5, or about 7.4). Useful buffers include saline-buffered phosphate or an ionic boric acid buffer. The active ingredient (e.g., any mRNA polymer complex or drug delivery system disclosed herein, such as included in a pharmaceutical and/or therapeutic composition), optionally together with excipients, can also be in the form of a lyophilizate and can be made into a solution prior to parenteral administration by the addition of suitable solvents. Solutions such as those that are used, for example, for parenteral administration by injection can also be used as infusion solutions.

In embodiments, pharmaceutical and/or therapeutic compositions disclosed herein can include an effective amount (e.g., a therapeutically effective amount) of any mRNA polymer complex or drug delivery system disclosed herein in a pharmaceutically acceptable carrier or excipient (e.g., an mRNA polymer complex or a drug delivery system that is dissolved or suspended in a pharmaceutically acceptable carrier or excipient). Exemplary pharmaceutically acceptable carriers and/or pharmaceutically acceptable excipients have been described (see, e.g., Kaczmarek et al., Genome Medicine, 9:60, 2017; Guild et al., WO 2012/170930; Remington's Pharmaceutical Sciences by E. W. Martin, Mack Publishing Co., Easton, Pa., 19th Edition (1995), all of which are incorporated herein by reference).

The nature of the carrier will depend on the particular mode of administration being employed. For example, parenteral formulations usually contain injectable or infusible fluids, such as pharmaceutically and physiologically acceptable fluids (e.g., water, physiological saline, balanced salt solutions, aqueous dextrose, glycerol, or the like) as a vehicle. In some examples, excipients can be included, such as proteins (e.g., human serum albumin) or plasma preparations. For solid compositions (e.g., powder, pill, tablet, or capsule forms), conventional non-toxic solid carriers can include, for example, pharmaceutical grades of mannitol, lactose, starch, or magnesium stearate. In addition, pharmaceutical compositions to be administered can contain minor amounts of non-toxic auxiliary substances, such as wetting or emulsifying agents, preservatives, pH buffering agents, and the like (e.g., sodium acetate or sorbitan monolaurate).

As used herein, "pharmaceutically acceptable carrier" includes any and all solvents, dispersion media, coatings, antibacterial and antifungal agents, isotonic and absorption delaying agents, and the like. The use of such media and agents for pharmaceutically active substances is well-known in the art. Except insofar as any conventional media or agent is incompatible with the active ingredient, its use in the pharmaceutical compositions is contemplated. Supplementary active ingredients also can be incorporated into the compositions. For example, dispersions can be prepared in glycerol, liquid polyethylene glycols, and mixtures thereof as well as in oils. Under ordinary conditions of storage and use, these preparations contain a preservative to prevent the growth of microorganisms.

In embodiments, the mRNA polymer complexes or drug delivery systems disclosed herein can form nanoparticles. In some examples, the nanoparticle can be formed by spontaneous electrostatic interaction between the negatively charged phosphate groups of mRNA and positively charged cationic polymer (e.g., the primary amines of a polyaspartic acid- or polyglutamic acid-DET polymer) between two or more mRNA polymer complexes. In some examples, the N/P ratio (positive polymer amine/negative mRNA phosphate) is at least about 1, 2, 3, 4, 5, 6, 7, or 8 or about 1-8, 2-5, 3-7, 4-6, 1-2, 2-3, 3-4, 4-5, 5-6, 6-7, or 7-8 or about 4. In some examples, the nanoparticles formed (e.g., with an N/P ratio of about 4) have a hydrodynamic diameter of at least about 45, 50, 60, 70, 80, 90, 100, 110, 120, or 130 nm or about 45-130, 50-110, 70-90, 45-50, 50-60, 60-70, 70-80, 80-90, 90-100, 100-110, 110-120, or 120-130 nm or about 80 nm.

The mRNA polymer complex or drug delivery system (e.g., as included in a pharmaceutical and/or therapeutic composition) can be formulated with or administered in conjunction with additional therapeutic agents. Exemplary agents include agents that treat conditions related to acute or chronic muscle atrophy and/or a muscle-wasting disease, such as sarcopenia, cachexia (e.g., megestrol, Megace®, Megace ES®, somatropin, Serostim®, and Norditropin FlexPro Pen®), cancer (e.g., carboplatin, Adriamycin®, Adrucil®, etoposide, fluorouracil, doxorubicin, Paraplatin®, Cosmegen®, cyclophosphamide, Ethyol®, Leukeran®, Vincasar PFS®, vincristine, Etopophos®, Oncovin®, Toposar®, Hycamtin®, Ifex®, ifosfamide, Mustargen®, Velban®, VePesid®, vinblastine, amifostine, chlorambucil, dactinomycin, mechlorethamine, Tepadina®, thiotepa, topotecan, and fludarabine), congestive heart failure (e.g., Furosemide®, Lasix®, carvedilol, Coreg®, spironolactone, Lisinopril®, digoxin, Metoprolol Succinate ER®, Aldactone®, Accupril®, metoprolol, isosorbide mononitrate, Coumadin®, Cardizem®, warfarin, Altace®, amlodipine, Lanoxin®, Norvasc®, Toprol-XL®, Nitrostat®, Diovan®, Prinivil®, Zestril®, diltiazem, hydralazine, nitroglycerin, Ramipril®, Apresoline®, bisoprolol, enalapril, torsemide, Vasotec®, isosorbide dinitrate, Lotensin®, allopurinol, Atacand®, Coreg®, valsartan, benazepril, Cardizem CD®, Cartia XT®, Digox®, Entresto®, Qbrelis®, quinapril, Cardizem LA®, CaroSpir®, Demadex®, Digitek®, Dilacor®, Dilt-XR®, Diltia XT®, Diltzac®, eplerenone, Jantoven®, Matzim LA®, nifedipine, Nitrolingual Pumpspray®, NitroQuick®, Taztia XT®, Tiadylt ER®, Tiazac®, candesartan, captopril, Clinacort®, dobutamine, hydrochlorothiazide/lisinopril, Isordil, Kenalog-40®, Lanoxicaps®, milrinone, Minitran®, Monoket®, Nitrek®, Nitro-Bid®, Nitro-Dur®, Nitro-Time®, Nitrocot®, Nitrol Appli-Kit®, NitroMist®, Nitro TD Patch-A®, Prexxartan®, Transderm-Nitro®, triamcinolone, amiloride, BiDil®, Capoten®, Corlanor®, Dobutrex®, hydrochlorothiazide/spironolactone, Inspra®, ivabradine, Midamor®, Minipress®, perindopril, prazosin, Prinzide®, sacubitril/valsartan, trandolapril, Zestoretic®, Aceon®, Aldactazide®, amiloride/hydrochlorothiazide, Capozide®, Capozide®, Capozide 25/25®, Capozide 50/15®, Capozide 50/25®, captopril/hydrochlorothiazide, Cardene®, Cardene IV®, Cardene SR®, Dilatrate-SR®, enalapril/hydrochlorothiazide, fosinopril, hydralazine/isosorbide dinitrate, Isochron®, IsoDitrate®, Isordil Titradose®, Mavik®, Moduretic 5-50®, moexipril, Monopril®, Natrecor®, nesiritide, nicardipine, Nipride RTU®, Nitropress®, nitroprusside, Primacor®, Univasc®, and Vaseretic®), renal failure (e.g., furosemide, Lasix®, Demadex®, Edecrin®, torsemide, Sodium Edecrin®, and ethacrynic acid), chronic obstructive pulmonary disease (e.g., Symbicort®, prednisone, montelukast, Breo Ellipta®, Daliresp®, Anoro Ellipta®, budesonide/formoterol, Tudorza Pressair®, Rayos®, aclidinium, fluticasone/vilanterol, Incruse Ellipta®, umeclidinium/vilanterol, roflumilast, Stiolto Respimat®, guaifenesin/theophylline, levalbuterol, olodaterol/tiotropium, dyphylline, olodaterol, Striverdi Respimat®, umeclidinium, Xopenex HFA®, Xopenex®, fluticasone/umeclidinium/vilanterol, Trelegy Ellipta®, and Xopenex Concentrate®), severe burns (e.g., silver sulfadiazine, Silvadene®, lidocaine, Xylocaine Jelly®, Bactine®, Dermoplast®, AneCream®, Solarcaine Burn Relief®, Albuminar-25®, Aloe Vera Burn Relief Spray with Lidocaine®, Lidocream®, Nupercainal®, SSD®, Xylocaine Topical®, Garamycin®, Thermazene®, Albutein®, AneCream with Tegaderm®, benzocaine, CidalEaze®, DermacinRx Lido V Pak®, Eha Lotion®, LidaMantle®, Lidopac®, Lidopin®, LidoRx®, LidoRxKit®, Lidotrans®, Lidovex®, Lidozion®, Lidozol®, Medi-Quik Spray®, RadiaGuard®, Regenecare HA Spray®, Senatec®, Sulfamylon®, Topicaine®, Vancocin®, Bionect®, gentamicin, vancomycin, mafenide, albumin human, dibucaine, Flexbumin®, Human Albumin Grifols®, Nebcin®, sodium hyaluronate, Tobi®, Tobramycin®, Vancocin HCl®, Vancocin HCl Pulvules®, Albuminar-5®, Albuminar-20®, SSD AF®, Albuked®, Albuked 5®, Albuked 25®, Albumin-ZLB®, Alburx®, Buminate®, Hylira®, IPM Wound®, Kedbumin®, Plasbumin®, Plasbumin-5®, Plasbumin-25®, RadiaPlex®, Solarcaine First Aid Medicated Spray®, and Xclair®), an inflammatory muscle disease, myasthenia gravis (e.g., Mestinon®, pyridostigmine, Mestinon Timespan®, azathioprine, mycophenolate mofetil, Prostigmin®, neostigmine, Prostigmin Bromide®, Regonol®, immune globulin intravenous, Soliris®, ephedrine, and eculizumab), neuropathy, polio (e.g., amantadine), multiple sclerosis (e.g., Copaxone®, Gilenya®, Ampyra®, Tysabri®, Tecfidera®, Aubagio®, Rebif®, Avonex®, Betaseron®, Decadron®, Prednisone®, Avonex Pen®, glatiramer, interferon beta-1a, fingolimod, dalfampridine, Novantrone®, dimethyl fumarate, teriflunomide, Acthar®, dexamethasone, Extavia®, natalizumab, Imuran®, Dexamethasone Intensol®, interferon beta-1b, prednisolone, Plegridy®, Prelone®, Rebif Rebidose®, valacyclovir, azathioprine, Lemtrada®, ocrelizumab, alemtuzumab, corticotropin, cyclophosphamide, Glatopa®, H.P. Acthar Gel®, mitoxantrone, peginterferon beta-1a, Azasan®, cladribine, daclizumab, De-Sone LA®, Dexpak Taperpak®, Millipred®, Millipred DP®, mycophenolate mofetil, Ocrevus®, Oraped®, PediaPred®, Veripred 20®, and Zinbryta®), anorexia nervosa (e.g., olanzapine and cyproheptadine), human immunodeficiency virus/acquired immune deficiency syndrome (e.g., non-nucleoside reverse transcriptase inhibitors, nucleoside analog reverse transcriptase inhibitors, and protease inhibitors), osteomalacia (e.g., vitamin D2, Drisdol®, ergocalciferol, Calciferol®, Calcidol®, Posture®, Ridactate®, calcium lactate, and calcium phosphate, tribasic), herniated disk, hypercalcemia, kwashiorkor, Creutzfeldt-Jakob disease or bovine spongiform encephalopathy (e.g., methylene blue, cefotaxime, and Claforan®), diabetes (e.g., Tresiba®, insulin degludec, insulin aspart/insulin degludec, and Ryzodeg 70/30®), amyotrophic lateral sclerosis (e.g., Rilutek®, riluzole, edaravone, and Radicava®), necrotizing vasculitis, abetalipoproteinemia, malabsorption syndrome, Legg-Calvé-Perthes disease, polymyositis (e.g., prednisone), Guillain-Barre syndrome, osteoarthritis (e.g., paracetamol, nonsteroidal anti-inflammatory drugs, antacid, COX-2 selective inhibitors, and glucocorticoids), and/or muscular dystrophy (e.g., deflazacort, eteplirsen, Emflaza®, Exondys 51®, mexiletine, phenytoin, procainamide, and nusinersen), such as Duchenne, Becker congenital, distal, myotonic, oculopharyngeal, Limb-Girdle, facioscapulohumeral, and/or Emery-Dreifuss muscular dystrophy.

Methods of Modulating Lean Muscle Mass in a Subject and Methods of Treatment

Methods of modulating lean muscle mass in a subject are disclosed herein. In embodiments, the methods include slowing the loss of, increasing, and/or maintaining lean muscle mass in a subject (e.g., a human and/or mammalian subject). In some examples, the methods include treating a subject with a muscle-wasting disease and/or muscle atrophy. In embodiments, the methods include administering to a subject an effective amount (e.g., a therapeutically effective amount) of any mRNA polymer complex or the drug delivery system disclosed herein (e.g., an mRNA polymer complex or drug delivery system that includes Formula I or Formula II, including an mRNA encoding follistatin). In embodiments, administering to the subject the mRNA polymer complex or the drug delivery system slows the loss of, increases, and/or maintains lean muscle mass in a subject and/or treats acute or chronic muscle atrophy and/or a muscle-wasting disease. The methods can include selecting a subject in need of augmented or maintained muscle growth, such as a subject with a muscle-wasting disease or muscle atrophy or a healthy subject, for example, to enhance athletic performance. Any type of subject can be selected, including human or mammalian subjects.

In some examples, the subject can have a muscle-wasting disease and/or acute or chronic muscle atrophy. The subject can have any muscle-wasting disease and/or any condition associated with acute or chronic muscle atrophy. In some examples, the subject can have sarcopenia, cachexia, cancer, congestive heart failure, renal failure, chronic obstructive pulmonary disease, severe burns, an inflammatory muscle disease, myasthenia gravis, neuropathy, polio, multiple sclerosis, anorexia nervosa, human immunodeficiency virus, acquired immune deficiency syndrome, osteomalacia, herniated disk, hypercalicemia, kwashiorkor, Creutzfeldt-Jakob disease, bovine spongiform encephalopathy, diabetes, amyotrophic lateral sclerosis, necrotizing vasculitis, abetalipoproteinemia, malabsorption syndrome, Legg Calvé-Perthes disease, muscular dystrophy, polymyositis, Guillain-Barre syndrome, and/or osteoarthritis.

The methods can include administering an mRNA polymer complex or a drug delivery system (e.g., subcutaneously) in any amount (e.g., any concentration and/or dose). The amount (e.g., concentration and/or dose) of the mRNA polymer complex or drug delivery system administered will depend on the subject being treated, the severity of the affliction, and the manner of administration and is best left to the judgment of the prescribing clinician. The mRNA polymer complex or drug delivery system can be administered at any concentration. Exemplary concentrations include at least about 10, 50, 100, 150, 200, 250, 300, 350, 400, 450, 500, 550, 600, 650, 700, 750, 800, 850, 900, 950, or 1000 ng/ml or about 10-1000, 25-500, 50-250, 100-500, 300-700, 400-800, 600-1000, 10-50, 50-100, 100-150, 150-200, 200-250, 250-300, 300-350, 350-400, 400-450, 450-500, 500-550, 600-650, 650-700, 700-750, 750-800, 800-850, 850-900, 900-950, or 950-1000 ng/ml or about 250 or 500 ng/ml. The mRNA polymer complex or drug delivery system can be administered at any dose. Exemplary doses include at least about 0.05, 0.1, 0.2, 0.3, 0.4, 0.5, 0.6, 0.7, 0.8, 0.9, 1, 2, or 5 mg/kg or about 0.05-1, 0.1-2, 0.5-5, 1-5, 2-4, 3-5, 0.05-0.1, 0.1-0.2, 0.2-0.3, 0.3-0.4, 0.4-0.5, 0.5-0.6, 0.6-0.7, 0.7-0.8, 0.8-0.9, 0.9-1, 1-2, or 2-5 mg/kg or about 0.5 mg/kg.

The methods can include administering an mRNA polymer complex or a drug delivery system over any timeframe. The timeframe of administration of the mRNA polymer complex or drug delivery system will depend on the subject being treated, the severity of the affliction, and the manner of administration and is best left to the judgment of the prescribing clinician. For example, the mRNA polymer complex or drug delivery system can be injected or infused over any length of time and/or the mRNA polymer complex or drug delivery system can be administered (e.g., by injection or infusion) in any amount of doses over any amount of time (e.g., as administered in the clinical trials cited in Kaczmarek et al., Genome Medicine, 9:60, 2017, including NCT01591356, NCT00938574, NCT01858935, NCT02227459, NCT02795325, NCT02706886, NCT02554773, NCT02352493, NCT02949830, NCT03060577, and NCT02900027, details for which can be found at clinicaltrials.gov, all of which are incorporated herein by reference). In some examples, the mRNA polymer complex or drug delivery system is infused, such as at least over about 1 minute, 5 minutes, 10 minutes, 15 minutes, 30 minutes, 45 minutes, 1 hour, 1.5 hours, 2 hours, 3 hours, 4 hours, 5 hours, 6 hours, 7 hours, or 8 hours or about 1-15 minutes, 2-30 minutes, 5-60 minutes, 15-90 minutes, 30-120 minutes, 5-10 minutes, 10-15 minutes, 15-30 minutes, 30-45 minutes, 45 minutes-1 hour, 1-1.5 hours, 1.5-2 hours, 2-3 hours, 3-4 hours, 4-5 hours, 5-6 hours, 6-7 hours, or 7-8 hours. In some examples, multiple doses of the mRNA polymer complex or drug delivery system can be administered (e.g., by injection or infusion, such as by subcutaneous injection), for example, at least about 1, 2, 3, 4, 5, 6, 7, 8, 9, 10, 12, 15, 18, 20, 25, 30, 35, 40, 45, or 50 doses or about 1-2, 2-3, 3-4, 4-5, 5-6, 6-7, 7-8, 8-9, 9-10, 10-12, 12-15, 15-18, 18-20, 20-25, 25-30, 30-35, 35-40, 40-45, or 45-50 doses or about 1 dose, 16 doses, or 18 doses. Exemplary frequencies for administering one or more doses of the mRNA polymer complex or drug delivery system include administration (e.g., injection or infusions, such as subcutaneous injection) at least about every day, 2 days, 3 days, 4 days, 5 days, 6 days, 7 days, 8 days, 9 days, 10 days, 30 days, 60 days, or 180 days or about every 1-7 days, 3-10 days, 5-14 days, 21-42 days, 28-60 days, 1 day-2 days, 2-3 days, 3-4 days, 4-5 days, 5-6 days, 6-7 days, 7-8 days, 8-9 days, 9-10 days, 10-30 days, 30-60 days, or 60-180 days or about every 3 days. Exemplary timespans for administering one or more doses of the mRNA polymer complex or drug delivery system include administering the doses over at least about 1 day, 3 days, 9 days, 18 days, 30 days, 60 days, 180 days, 1 year, 2 years, 3 years, or 4 years or about 1 day-3 days, 3-9 days, 9-18 days, 18-30 days, 30-60 days, 60-180 days, 180 days-1 year, 1-2 years, 2-3 years, or 3-4 years or about 1 days or 60 days. In some examples, the mRNA polymer complex or drug delivery system can be administered (e.g., by subcutaneous injection, such as every 3 days) indefinitely, such as to a subject with chronic muscle atrophy and/or a chronic muscle-wasting disease.

In embodiments, the methods include assessing biocompatibility (e.g., efficacy, therapeutic response, toxicity, inflammation, side effects, and/or elimination), such as before, with, and/or after administration of an mRNA polymer complex or a drug delivery system disclosed herein. In some examples, efficacy and/or therapeutic response is assessed. Assays for efficacy and/or therapeutic response are known in the art. Any efficacy and/or therapeutic response assay can be used. Exemplary efficacy and/or therapeutic response assays include measuring levels of molecules involved in forming muscle mass, such as follistatin, myostatin, and/or activin A levels. Levels of molecules involved in forming muscle mass can be measured in any fluid or tissue, such as in a urine or blood sample (e.g., whole blood, serum, and/or plasma). Any method of measuring such molecules can be used (e.g., immunohistochemistry, IHC). In some examples, efficacy and/or therapeutic response is assessed by measuring physiological changes, such as changes in body fat and/or muscle mass. Any method of measuring physiological changes can be used (e.g., Correa-de-Araujo, Front Physiol., 8:87, 2017, incorporated herein by reference). In some examples, measurements in an efficacy and/or therapeutic response assay can be compared to measurements and/or expected measurements in a control subject (e.g., a subject that was not administered an mRNA polymer complex or a drug delivery system disclosed herein).

In some examples, the methods herein include an increase in the follistatin levels (e.g., blood levels, such as blood serum levels) of a subject by at least about 0.5-, 1-, 1.5-, 2-, 2.5-, 3-, 3.5-, 4-, 4.5-, 5-, 5.5-, 6-, 6.5-, 7-, 7.5-, or 8-fold or about 0.5- to 1-fold, 1- to 1.5-fold, 1.5- to 2-fold, 2- to 2.5-fold, 2.5- to 3-fold, 3- to 3.5-fold, 3.5- to 4-fold, 4- to 4.5-fold, 4.5- to 5-fold, 5- to 5.5-fold, 5.5- to 6-fold, 6- to 6.5-fold, 6.5- to 7-fold, 7- to 7.5-fold, or 7.5- to 8-fold or about 1.8-, 2.1-, or 2.4-fold (e.g., after administration of an mRNA polymer complex or a drug delivery system disclosed herein, such as at least about 2, 4, 8, 12, 24, 48, 72, 96, or 120 hours or about 2-4, 4-8, 8-12, 12-24, 24-48, 48-72, 72-96, or 96-120 hours or about 8 or 24 hours after administration of a disclosed mRNA polymer complex or drug delivery system, for example, about 0.5 mg/kg thereof). In some examples, the methods herein include increasing the blood levels (e.g., blood serum levels) of follistatin for at least about 1 hour, 2 hours, 4 hours, 8 hours, 12 hours, 1 day, 2 days, 3 days, 4 days, 5 days, 6 days, or 7 days or about 1 hour-2 hours, 2-4 hours, 4-8 hours, 8-12 hours, 12 hours-1 day, 1-2 days, 2-3 days, 3-4 days, 4-5 days, 5-6 days, or 6-7 days or at least about 3 days after administration of a dose of an mRNA polymer complex or a drug delivery system disclosed herein (e.g., after administration of 1 or more doses thereof).

In some examples, the methods herein include a decrease in the blood levels (e.g., blood serum levels) of myostatin and/or activin A by at least about 0.5-, 1-, 1.5-, 2-, 2.5-, 3-, 3.5-, 4-, 4.5-, 5-, 5.5-, 6-, 6.5-, 7-, 7.5-, or 8-fold or about 0.5- to 1-fold, 1- to 1.5-fold, 1.5- to 2-fold, 2- to 2.5-fold, 2.5- to 3-fold, 3- to 3.5-fold, 3.5- to 4-fold, 4- to 4.5-fold, 4.5- to 5-fold, 5- to 5.5-fold, 5.5- to 6-fold, 6- to 6.5-fold, 6.5- to 7-fold, 7- to 7.5-fold, or 7.5- to 8-fold or about 1.8-fold (e.g., after administration of an mRNA polymer complex or a drug delivery system disclosed herein, such as at least about 2, 4, 8, 12, 24, 48, 72, 96, or 120 hours or about 2-4, 4-8, 8-12, 12-24, 24-48, 48-72, 72-96, or 96-120 hours after administration of a disclosed mRNA polymer complex or drug delivery system, for example, about 0.5 mg/kg thereof).

In some examples, the methods herein include physiological changes, such as changes in body fat and/or muscle mass, in a subject. In some examples, changes (e.g., a decrease) in body fat are observed, such as a change (e.g., a decrease) of at least about 1, 2, 5, 10, 15, 20, 25, 30, 35, 40, 45, or 50% or about 1-2, 2-5, 5-10, 10-15, 15-20, 20-25, 25-30, 30-35, 35-40, 40-45, or 45-50% or about 25% (e.g., after administration of an mRNA polymer complex or a drug delivery system disclosed herein), such as at least about 2, 4, 8, 12, 24, 48, 72, 96, or 120 hours or about 2-4, 4-8, 8-12, 12-24, 24-48, 48-72, 72-96, or 96-120 hours after administration of a disclosed mRNA polymer complex or drug delivery system, for example, about 0.5 mg/kg thereof. In some examples, changes (e.g., an increase) in muscle mass are observed, such as a change (e.g., an increase) of at least about 1, 2, 3, 4, 5, 6, 7, 8, 9, 10, 15, 20, or 25% or about 1-2, 2-3, 3-4, 4-5, 5-6, 6-7, 7-8, 8-9, 9-10, 10-15, 15-20, or 20-25% or about 10% (e.g., after administration of an mRNA polymer complex or a drug delivery system disclosed herein), such as at least about 2, 4, 8, 12, 24, 48, 72, 96, or 120 hours or about 2-4, 4-8, 8-12, 12-24, 24-48, 48-72, 72-96, or 96-120 hours after administration of a disclosed mRNA polymer complex or drug delivery system, for example, about 0.5 mg/kg thereof.

In some examples, side effects and/or toxicity is assessed. Side effect and toxicity assays are known in the art (see, e.g., Mendell et al., Mol Ther., 23(1):192-201, 2015; Haidet et al., Proc Natl Acad Sci USA, 105(11):4318-22, 2008; Rodina-Klapac et al., Muscle Nerve., 39(3):283-96, 2009). Any assays for side effects and toxicity can be used. Exemplary toxicity assays include measuring molecules associated with toxicity (e.g., toxicity-associated biomarkers), such as molecules associated with liver, kidney, muscle, heart, and/or major organ toxicity, in a subject and comparing the measured values to those expected from a control subject without toxicity.

In some examples, toxicity assays can include liver toxicity assays, such as measuring alkaline phosphatase (ALP), alanine aminotransferase (ALT), aspartate transferase (AST), gamma-glutamyl transferase (GGT), and/or bilirubin levels (see, e.g., Giannini et al., CMAJ, 172(3): 367-379, 2005, incorporated herein by reference). Levels of ALP, ALT, AST, GGT, and bilirubin typically increase under conditions of liver toxicity. In some examples, the methods include administration of an mRNA polymer complex or a drug delivery system disclosed herein without an increase (such as without a statistically significant increase) in ALP, ALT, AST, GGT, and/or bilirubin (e.g., the disclosed mRNA polymer complex or drug delivery system is non-toxic). In other examples, an increase in ALP, ALT, AST, GGT, and/or bilirubin is within clinically acceptable limits.

In some examples, toxicity assays can include kidney toxicity assays, such as measuring blood urea nitrogen (BUN), creatinine levels, urinary proteins with enzymatic activity, proteinuria, kidney injury molecule-1 (KIM-1), neutrophil gelatinase-associated lipocalin (NGAL), cytokines, clusterin, osteopontin, and/or type IV collagen (see, e.g., Kim and Moon, Biomol Ther (Seoul), 20(3): 268-272, 2012, incorporated herein by reference). Levels of BUN, creatinine, urinary proteins with enzymatic activity, proteinuria, KIM-1, NGAL, cytokines, clusterin, oseopontin, and/or type IV collagen typically increase under conditions of kidney toxicity. In some examples, the methods include administration of an mRNA polymer complex or a drug delivery system disclosed herein without an increase (such as without a statistically significant increase) in BUN, creatinine, urinary proteins with enzymatic activity, proteinuria, KIM-1, NGAL, cytokines, clusterin, oseopontin, and/or type IV collagen (e.g., the disclosed mRNA polymer complex or drug delivery system is non-toxic). In other examples, an increase in BUN, creatinine, urinary proteins with enzymatic activity, proteinuria, KIM-1, NGAL, cytokines, clusterin, oseopontin, and/or type IV collagen is within clinically acceptable limits.

In some examples, toxicity assays can include muscle and/or heart toxicity assays, such as measuring creatine kinase (CK), AST, skeletal troponin I (Tnni1, Tnni2), skeletal troponin T (Tnnt1, Tnnt3), creatinine kinase protein M, parvalbumin (Pvalb), myosin light chain 3 (My13), fatty acid-binding protein 3 (Fabp3), aldolase A (Aldoa), and/or myoglobin, including myoglobinuria (see, e.g., Campion et al., Expert Opin Drug Metab Toxicol, 9(11), doi:10.1517/17425255.2013.827170, 2013, incorporated herein by reference). Levels of CK, AST, Tnni1 (or Tnni2), Tnnt1 (or Tnnt3), creatinine kinase protein M, Pvalb, My13, Fabp3, Aldoa, and/or myoglobin typically increase under conditions of muscle or heart toxicity. In some examples, the methods include administration of an mRNA polymer complex or a drug delivery system disclosed herein without an increase (such as without a statistically significant increase) in CK, AST, Tnni1 (or Tnni2), Tnnt1 (or Tnnt3), creatinine kinase protein M, Pvalb, My13, Fabp3, Aldoa, and/or myoglobin (e.g., the disclosed mRNA polymer complex or drug delivery system is non-toxic). In other examples, an increase in CK, AST, Tnni1 (or Tnni2), Tnnt1 (or Tnnt3), creatinine kinase protein M, Pvalb, My13, Fabp3, Aldoa, and/or myoglobin is within clinically acceptable limits.

In some examples, toxicity assays can include major organ toxicity assays, such as measuring blood protein and/or electrolyte levels (e.g., in whole blood, serum, and/or plasma). In general, changes in electrolyte levels and increases in protein levels are associated with major organ toxicity. In some examples, the methods include administration of an mRNA polymer complex or a drug delivery system disclosed herein without a change in electrolyte levels and/or an increase in protein levels (such as without a statistically significant increase) (e.g., the disclosed mRNA polymer complex or drug delivery system is non-toxic). Other indicia of toxicity (e.g., toxicity-associated biomarkers) are possible (see, e.g., Campion et al., Expert Opin Drug Metab Toxicol, 9(11), doi:10.1517/17425255.2013.827170, 2013; Anadón et al., Chapter 34. Biomarkers of drug toxicity. Biomarkers in Toxicology, 593-607, 2014, both of which are incorporated herein by reference). In other examples, changes in electrolyte levels and/or protein levels is within clinically acceptable limits.

In some examples, inflammation is assessed. Inflammation assays are known in the art. Any inflammation assay can be used. Exemplary inflammation assays include measuring molecules associated with inflammation (e.g., inflammation-associated molecules), such as expression of inflammatory genes, in a subject and comparing the measured values to those expected from a control subject without inflammation. In some examples, inflammation assays include measuring expression of tumor necrosis factor (TNF), interleukin (IL)-6, IL-1b, C-reactive protein (CRP), and/or adenomatous polyposis coli (APC) genes. In some examples, the methods include administration of an mRNA polymer complex or a drug delivery system disclosed herein without a change (such as without a statistically significant change) in TNF, IL-6, IL-1b, CRP, and/or APC gene expression (e.g., the disclosed mRNA polymer complex or drug delivery system is non-inflammatory). Expression levels of other inflammatory genes can also be assessed (see, e.g., Cooper et al., Genome Biol., 6(1): R5, 2005; Newton and Dixit, Cold Spring Harb Perspect Biol, 4(3):pii: a006049, 2012, both of which are incorporated herein by reference).

In some examples, elimination of the mRNA polymer complex or a drug delivery system is assessed. Any method of assessing elimination can be used (e.g., measuring the half-life and/or clearance rate; see, e.g., Gidal et al., Epilepsy Research, 129:26-32, 2017, incorporated herein by reference). In specific examples, the methods include measuring the half-life of the mRNA polymer complex or a drug delivery system. In some examples, the methods include administering the mRNA polymer complex or a drug delivery system and measuring a half-life of at least about 12, 16, 24, 36, 48, 60, 72, 84, or 96 hours or about 12-16, 16-24, 24-36, 36-48, 48-60, 60-72, 72-84, or 84-96 hours or about 72 hours.

EXAMPLES

The following examples relate to compositions and methods useful for preventing or reversing lean muscle mass loss resulting from a muscle wasting disease or to augmenting muscle growth in a healthy subject.

Using messenger RNA (mRNA) to increase or upregulate protein synthesis is an emerging and underutilized treatment option. The following examples describe a non-viral delivery method that can circumvent the limitations of using a viral vector delivery and cDNA as a therapeutic treatment option. In the following examples, a non-viral delivery method using mRNA that codes for follistatin (FS) protein complexed to a biodegradable non-toxic delivery system for increasing lean muscle mass is described.

The examples demonstrate mRNA loading and biocompatibility of a non-viral, polyamino acid cationic polymer for in vitro and in vivo delivery of FS mRNA. Internalization, production, and secretion of the FS protein was evaluated in vitro using cultured hepatocytes, and in vivo using a non-immunocompromised Swiss Webster mouse model. The examples herein demonstrate that delivery of the FS mRNA nanoparticle drug delivery system (mRDDS), which comprises a mRNA polymer complex of the present disclosure results in hepatocyte and liver accumulation, as an increase in FS was observed in both the cell culture media and in the blood serum. The examples further demonstrate an observed and maintained increase in body weight above the non-treated control group following an every three day subcutaneous injection regimen of the mRDDS over a month's time period.

The following examples are illustrative of disclosed embodiments. In light of this disclosure, those of skill in the art will recognize that variations of these examples and other examples of the disclosed technology would be possible without undue experimentation.

Figure 3:
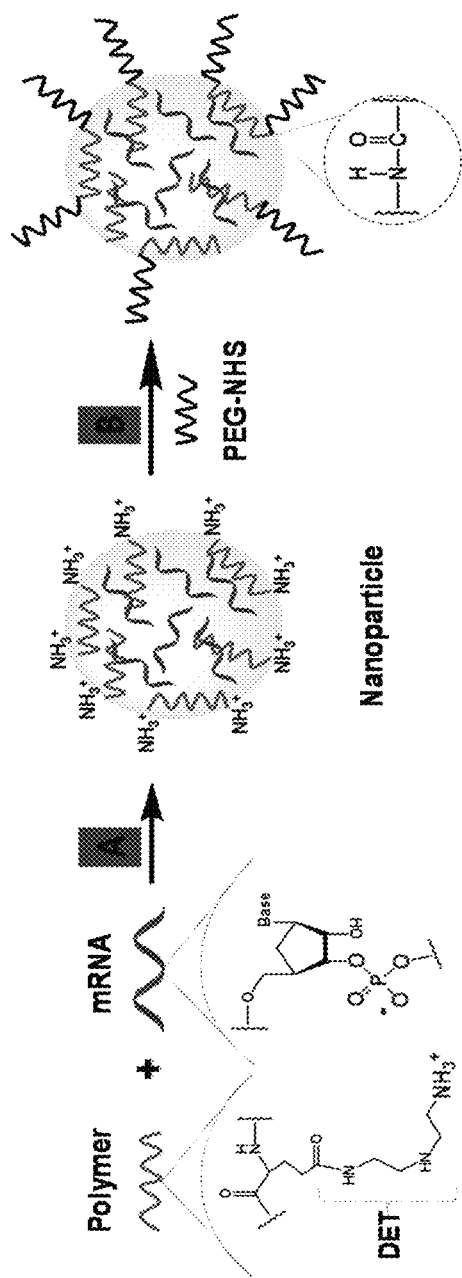
FIG. 3 is a schematic diagram showing an exemplary method of preparing mRNA-loaded polymeric nanoparticles. Negatively charged FS-344 mRNA undergo complexation (step A) by positively charged P[Glu(DET)] polymers into nanoparticles. The mRNA-loaded nanoparticles are modified (step B) by conjugation of PEG to polymer amino groups on the nanoparticle surface via an amide bond.
Figures 4A, 4B, 4C, 4D, 4E, 4F:
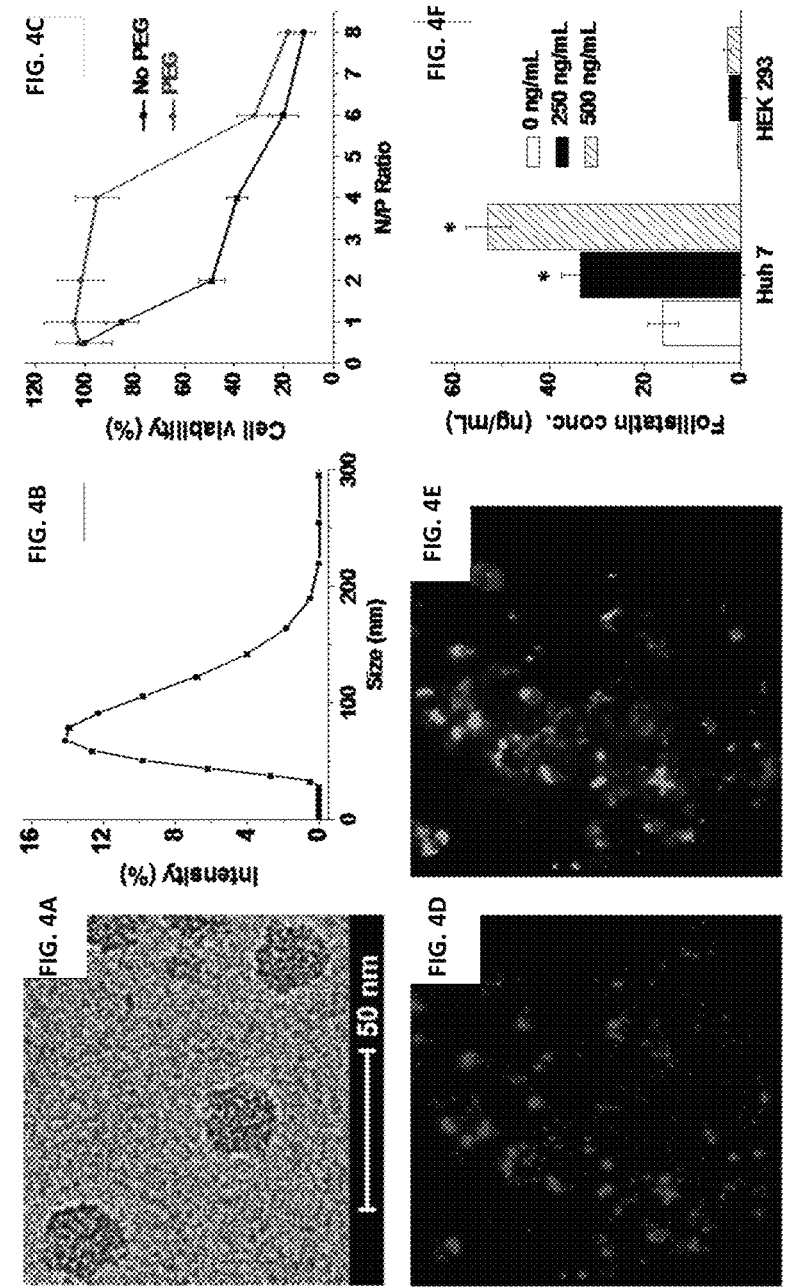
FIGS. 4A-4F show a representative cryoTEM image (FIG. 4A) and a dynamic light scattering profile (FIG. 4B) of the PEG-modified, mRNA-loaded nanoparticles.
Figure 10:
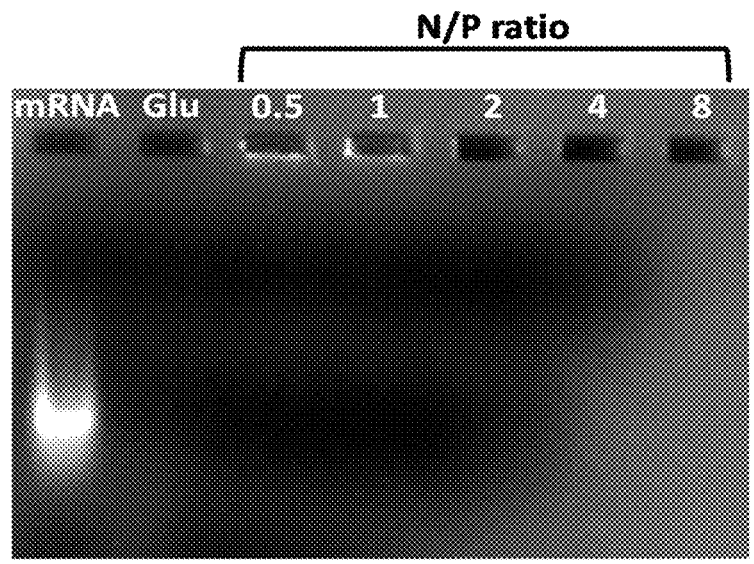
FIG. 10 shows a representative gel electrophoresis image of free mRNA, N-substituted polyglutamide (P[Glu(DET)] or Glu), and nanoparticles prepared by mixing mRNA with the employed polymer at the following N/P ratios of 0.5, 1, 2, 4, and 8. Efficient binding of mRNA molecules with the polymer retards gel electrophoretic mobility and prevents mRNA staining by ethidium bromide compared with free mRNA.

Example 1. Preparation and In Vitro Characterization of mRNA-Loaded Nanoparticles mRNA-loaded polymeric nanoparticles were prepared by complexation of FS-344 (SEQ ID NO: 1) mRNA and N-substituted polyglutamide (P[Glu(DET)]) containing 1,2-diaminoethane (DET) as side chains (FIG. 3, step A). The employed P[Glu(DET)] composed of 80 repeating units (MW=24,000) was synthesized and characterized (Itaka et al., Biomaterials, 31:3707-3714, 2010). A gel retardation assay validated high efficiency of P[Glu(DET)] complexing with mRNA at various N/P (positive polymer amine/negative mRNA phosphate) ratios via a spontaneous electrostatic interaction between negatively charged phosphate groups of the mRNA and positively charged primary amines of the DET (FIG. 10). The protonated amines in the polymer structure (FIG. 3, step A), which are important for mRNA complexation, introduced a positive charge onto the surface of the nanoparticles (+19.2±3.7 mV). To diminish toxicity associated with high positive charge and improve biocompatibility of the prepared nanoparticles, the nanoparticle surfaces were modified with a polyethylene glycol (PEG, 2 kDa) by coupling NHS groups located on the terminal end of PEG to DET amines on the nanoparticle surface via amide bonds (FIG. 3, step B). The final nanoparticles prepared at an N/P ratio of 4 had a slightly positive surface charge (+4.3±1.5 mV), spherical shape (FIG. 4A), a hydrodynamic diameter of 80.0±1.5 nm (FIG. 4B), a relatively narrow size distribution (polydispersity index (PDI)=0.23±0.02), and contained 100 µg of mRNA per 93.6 µg of the polymer. In contrast to non-modified nanoparticles, nanoparticles prepared at an N/P ratio≤4 and coated with PEG did not compromise the viability of the liver cells (FIG. 4C). In vitro studies further confirmed that the nanoparticles effectively delivered the encapsulated mRNA into hepatic cells, and the released mRNA molecules were translated into a corresponding protein. After a 48-h incubation period of Huh 7 cells with the nanoparticles containing Cy5-labeled mRNA coding for a green fluorescent protein (GFP), strong red (Cy5) and green (GFP) fluorescence signals were detected in the cells (FIGS. 4D and 4E). To verify that the delivered FS-344 mRNA was capable of follistatin protein production and controlling the protein concentrations in a dose-dependent manner, cells were incubated for 48 h with the nanoparticles at two different concentrations of FS-344 mRNA (250 and 500 ng/mL) and analyzed for follistatin secretion in the cell culture media using an ELISA assay. When compared with non-treated cells (0 h), 2.1- and 3.3-fold increases in follistatin protein secretion were detected after incubation of hepatocytes with nanoparticles loaded with low and high mRNA concentrations, respectively (FIG. 4F).

Figure 5:
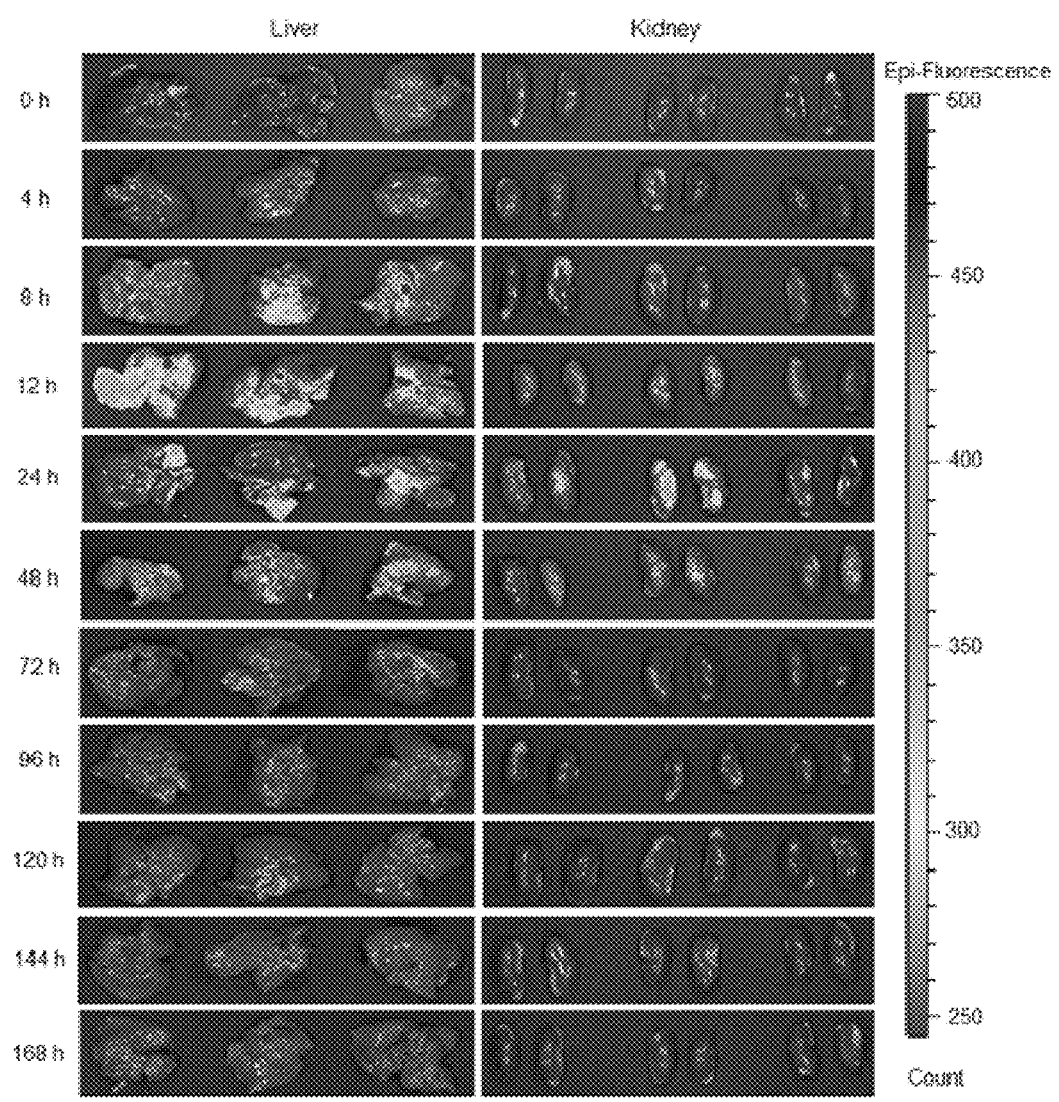
FIG. 5 shows GFP production in the livers and kidneys at various time points following SubQ injection of the nanoparticles loaded with GFP mRNA at a dose of 0.5 mg/kg.
Figure 11:
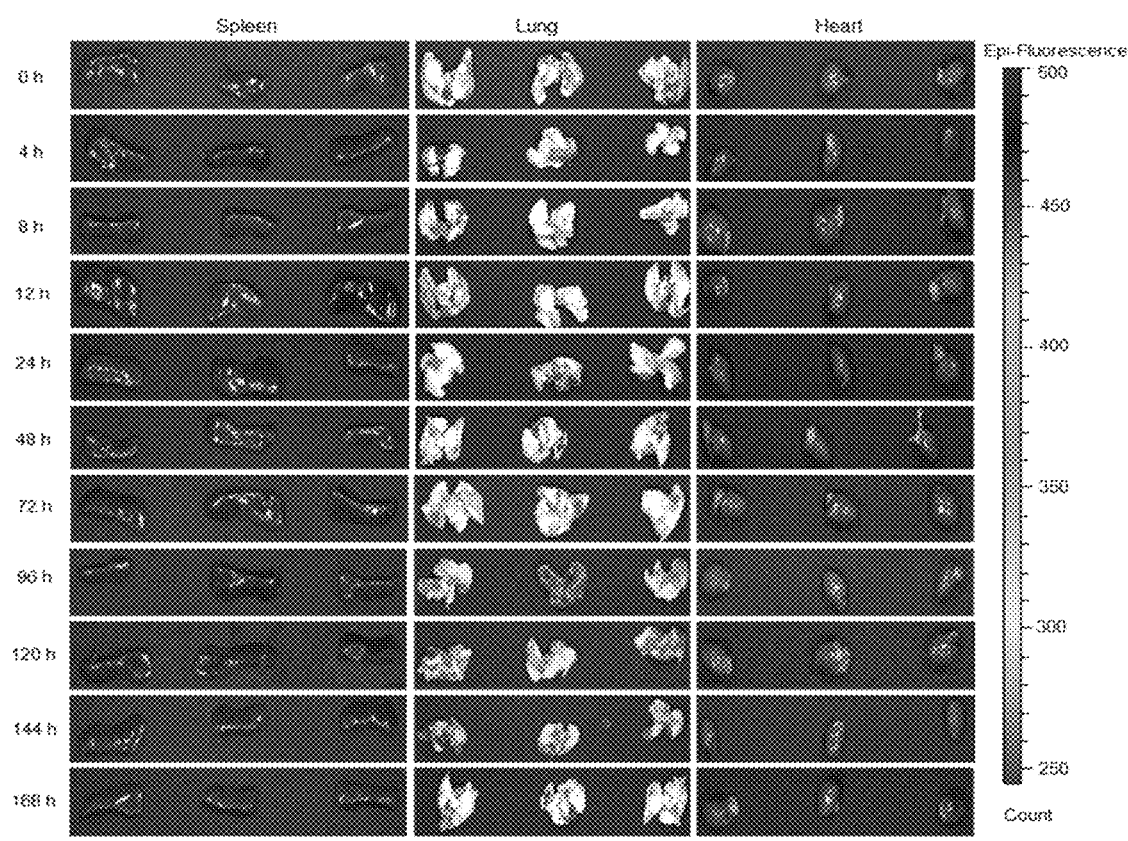
FIG. 11 shows GFP production in the spleens, lungs, and hearts at various time points following SubQ injection of the nanoparticles loaded with GFP mRNA at a dose of 0.5 mg/kg.
Figure 12:
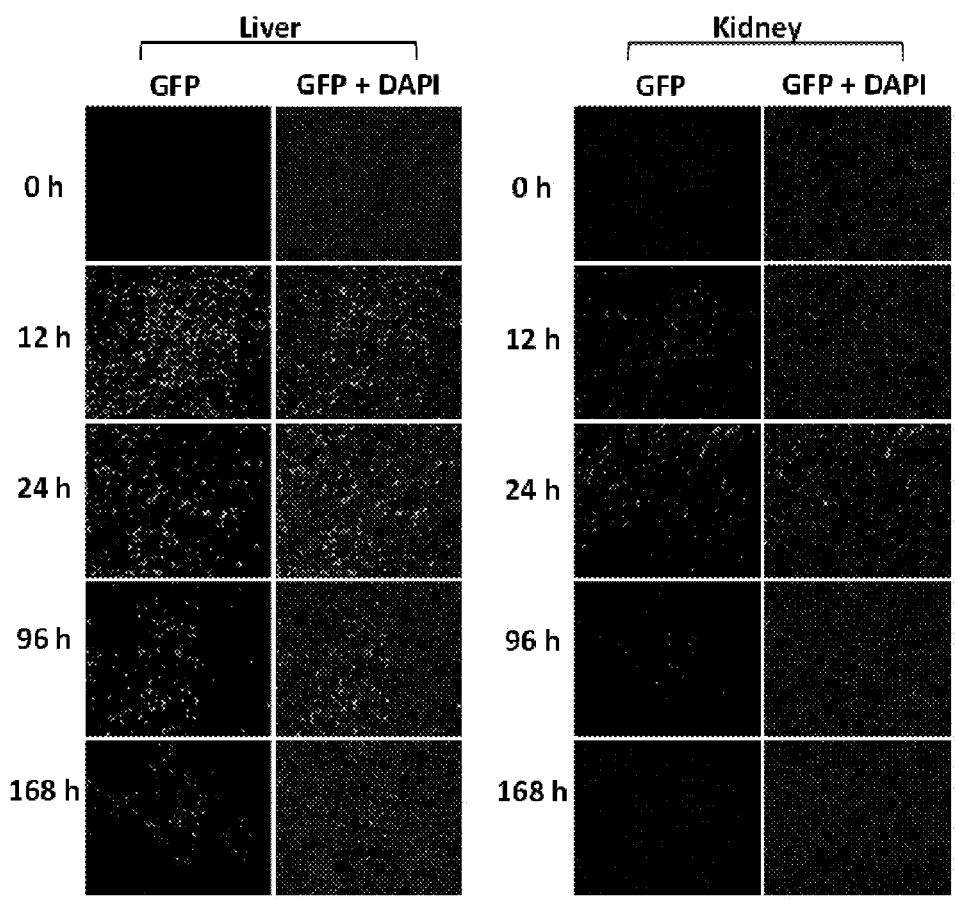
FIG. 12 shows representative fluorescence images of the liver and kidney cross-sections harvested from the mice at the various time points following SubQ injection of the nanoparticles loaded with GFP mRNA at a dose of 0.5 mg/kg. Fluorescence signals generated by the expressed GFP and DAPI-stained nuclei are shown.

Example 2. Evaluation of Biodistribution, Protein Production Efficiency, and Acute Toxicity of the mRNA-Loaded Nanoparticle To assess biodistribution and protein production, mice were injected subcutaneously (SubQ) with a single dose of GFP mRNA-loaded nanoparticles, and organs were collected at 4, 8, 12, 24, 48, 72, 96, 120, 144, and 168 h post injection. At each time point, the GFP production and biodistribution were evaluated by measuring green fluorescence intensity with the IVIS imaging system in various organs. The fluorescent signal was only detected in the livers and kidneys (FIG. 5 and FIG. 11), and the intensity of GFP fluorescence was significantly higher and prolonged in the liver when compared to kidneys. The fluorescence signal was observed in the livers as early as 4 h after injection, reached a maximum intensity at 12 h, and remained detectable at 168 h post-injection. In contrast, minimal fluorescence was detected in the kidneys only 12 h after administration, reached a maximum intensity at 24 h, and disappeared at 72 h (FIG. 5). The regions of interest were drawn over the livers and kidneys, and the average fluorescence signal for each organ was measured using IVIS Imaging System software. Quantitative analysis revealed that fluorescence intensity in the livers at 12 h post injection was 4.3 times higher compared with the fluorescence signal in the kidneys at 24 h, when the fluorescence signal was maximal. The livers and kidneys were embedded in paraffin, sectioned, and collected onto slides. Fluorescence imaging of the tissue sections confirmed the results obtained with the IVIS Imaging System (FIG. 12). The in vitro data supports animal studies demonstrating that the liver cells outperformed the kidney cells by providing a 20-fold increase in protein production (FIG. 4F).

Figure 6A:
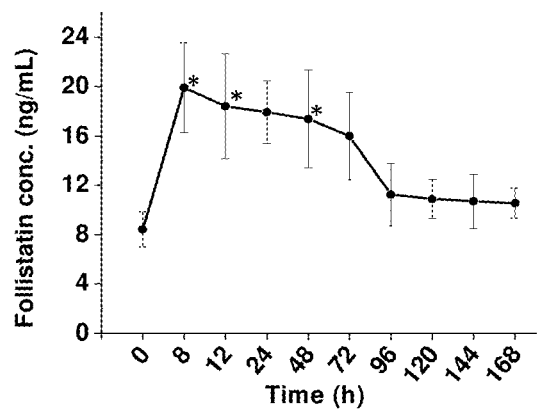
FIGS. 6A-6B show follistatin levels of mice.

To evaluate efficacy of the nanoplatform for increasing serum follistatin levels, mice were SubQ injected with a single dose of polymeric nanoparticles loaded with FS-344 mRNA at a dose of 0.5 mg/kg. Blood samples were collected before and at various time points post injection, and follistatin serum concentrations were analyzed with an ELISA kit. Follistatin serum levels increased by 2.4-fold eight hours after injection (FIG. 6A), and the elevated follistatin levels persisted up to 72 h. A minimal decrease (3.9 ng/mL) of follistatin serum levels was observed from the 8 h time point (19.9 ng/mL) until the 72 h time point (16.0 ng/mL). This result correlates well with in vivo biodistribution data (FIG. 5). Follistatin levels returned to baseline at approximately 96 h because follistatin is secreted and is not an intracellular protein; therefore, clearance is greater.

Figure 6B:
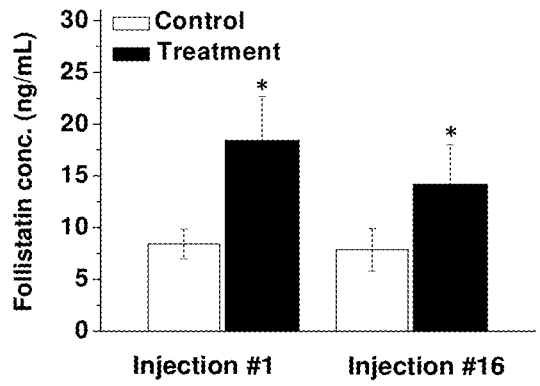

Because follistatin gene therapy requires multiple repeat administrations, separate studies were performed to validate the efficiency of PEG-modified nanoparticles at elevating serum follistatin levels after 16 repeated injections. The mice were SubQ injected with FS-344 mRNA-loaded nanoparticles (Example 1) every 72 hours for 8 weeks, and follistatin serum concentrations were measured 24 h after the first and last injections. The increases in follistatin serum levels were 2.1- and 1.8-fold following the first and last injections, respectively (FIG. 6B).

Figure 7A:
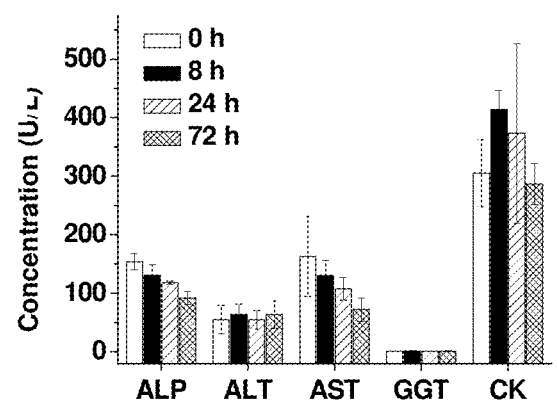
FIGS. 7A-7C show blood levels of certain proteins assessed at different time points. For non-treated mice (0 h) and mice SubQ injected with the FS-344 mRNA loaded nanoparticles (0.5 mg/kg) assessed after different time points.
Figure 7B:
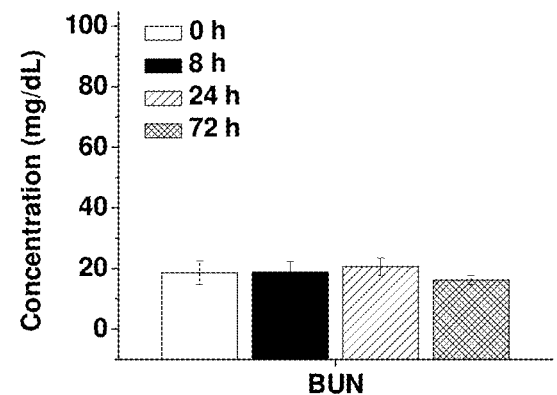
Figure 7C:
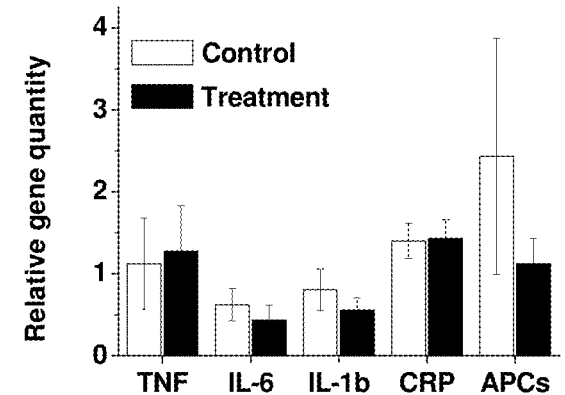
Figure 13A:
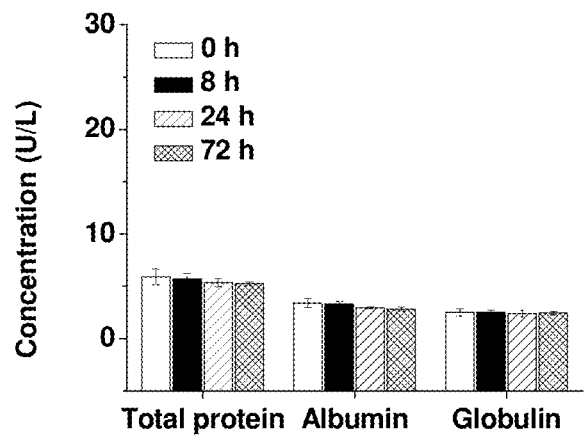
FIGS. 13A-13C show the blood levels of total protein, albumin and globulin (FIG. 13A) and total carbon dioxide ($tCO_2$) and electrolytes (chloride (Cl), potassium (K), sodium (Na), calcium (Ca), phosphorus (P)
Figure 13B:
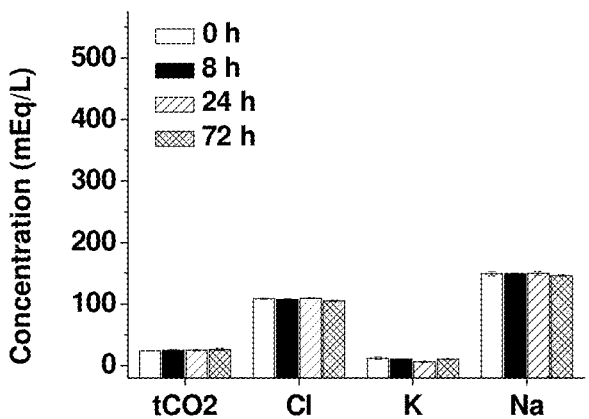
Figure 13C:
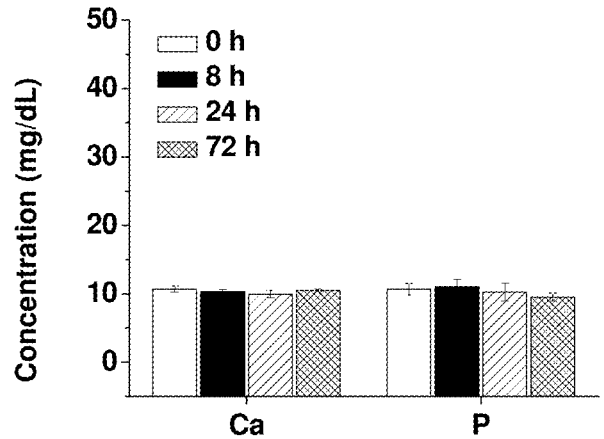

Despite accumulation of the developed nanoplatform in the liver and kidney and efficient production of secreted follistatin protein, mice did not display any signs of toxicity (e.g., a change in behavior, appearance, etc.) after SubQ injection of the nanoparticles loaded with FS-344 mRNA (0.5 mg/kg). To evaluate the effect of nanoparticles and follistatin production on acute liver, renal, and muscle toxicity, surrogate biomarker concentrations were measured in the blood for liver function (ALP, ALT, AST, and GGT), muscle and heart function (CK), and kidney function (BUN) (FIGS. 7A and 7B). In addition, the serum levels of proteins and blood electrolytes were evaluated as an indicator of major organ toxicity (FIGS. 13A-13C) (Shah et al., J Control Release, 253:37-45, 2017). The values measured in the mice treated with the FS-344 mRNA-loaded nanoparticles at various time points post-injection were not higher compared with non-treated mice (0 h). Finally, to detect any liver inflammation with the developed therapy, expression of select inflammatory genes was measured for mouse livers after 16 repeated injections of the FS-344 mRNA-loaded nanoparticles. A significant increase in the tested inflammatory genes was not detected in the liver of the treated mice compared with the control group (FIG. 7C).

Example 3. Evaluation of Nanoparticle Efficiency to Increase Lean Muscle Mass

After evaluating toxicity and determining a dosing schedule, wild type 17-week-old C57BL/6L mice were used to assess efficiency of the developed mRNA therapy at increasing lean muscle mass. The rationale for utilizing a post-adolescence model was to monitor changes in the lean and fat body mass as an adult with a static body composition rather than treating younger mice whose growth could be attributed to adolescent-induced anabolic growth. A previous report showed growth curves of 3-14 weeks C57BL/6L mice that show a typical weight gain range of approximately 1-6 grams per week (jax.org). In the subsequent weeks 15-20, a plateau effect with weight gain averaging only approximately 0.3 grams per week was observed, which indicates adult growth quiescence (jax.org).

Figures 8A, 8B, 8C, 8D:
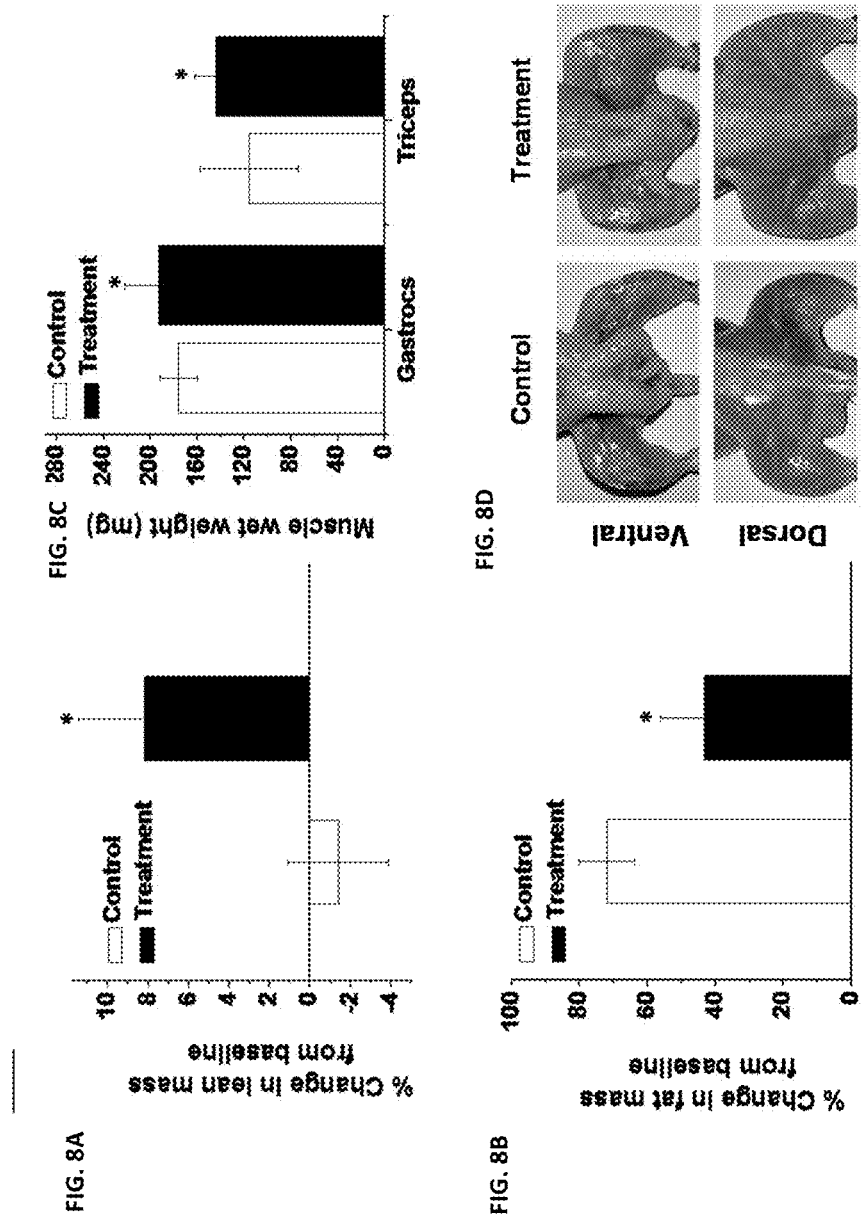
FIGS. 8A-8D show measurements for mice treated with FS-344.

After baseline muscle and fat mass were measured by magnetic resonance relaxometry (EchoMRI), mice in the control and treatment groups were SubQ injected every three days during eight weeks with saline or the nanoparticles loaded with FS-344 mRNA (Example 1; 0.5 mg/kg), respectively. Animals were then monitored, and body composition (lean and fat mass) was measured. After 8 weeks of treatment, the lean mass content of the mice in the treatment group was 8.2% higher than their baseline values (FIG. 8A). In contrast, the lean muscle mass content of the animals in the control group decreased by 1.4% during the same period of time (FIG. 8A). A body composition analysis further demonstrates, after the eight-week treatment regimen, body fat was 28.6% lower in the nanoparticle-treated mice compared with the non-treated controls, indicating that follistatin is also directly or indirectly involved in regulating fat metabolism (FIG. 8B). Gastrocnemius and triceps muscles were excised at the end of treatment cycle, and wet weight was measured. The gastrocnemius and triceps wet weights were 9.6% and 23.9% greater in treated mice compared with the control group (FIG. 8C), demonstrating that administration of mRNA-loaded nanoparticles stimulated muscle mass gain. Gross observation of nanoparticles-treated animals also demonstrated an increase in muscle size compared with controlled animals (FIG. 8D).

Figure 9A:
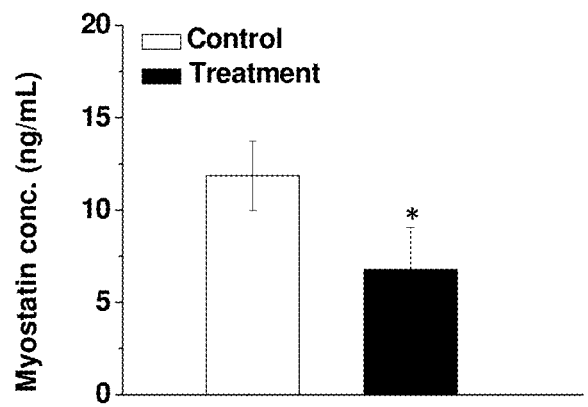
FIGS. 9A-9C show myostatin and activin A concentrations as well as tissue weight in mice treated with FS-344. Serum levels of myostatin (FIG. 9A) and activin A (FIG. 9B) after eight weeks of treatment with saline (control) or FS-344 mRNA-loaded nanoparticles (treatment). Serum concentrations of myostatin and activin A were analyzed using an ELISA assay. *$P<0.05$ when compared with protein levels in the serum of non-treated animals.
Figure 9B:
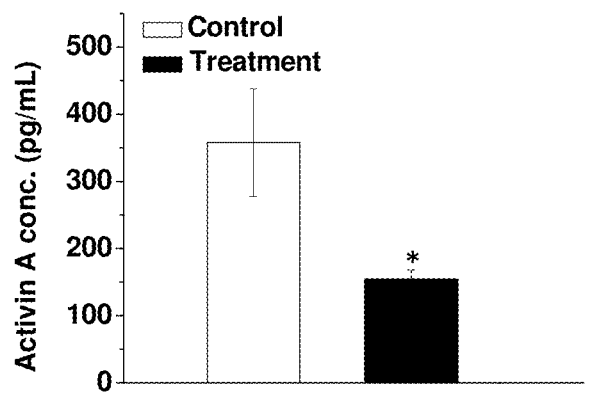
Figure 9C:
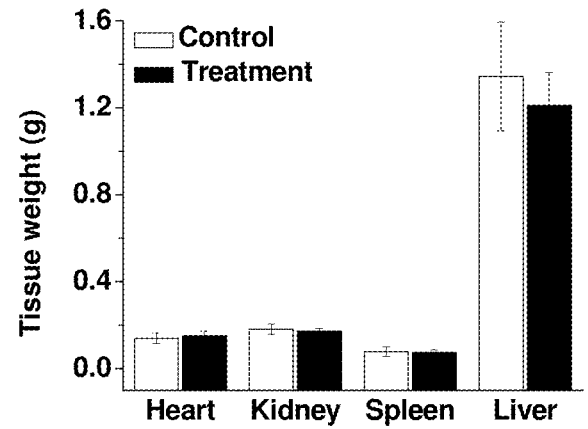

An analysis of blood samples at the end of treatment revealed that the serum levels of activin A and myostatin in mice treated with mRNA-loaded nanoparticles were 1.8 times lower compared with the control animals (FIGS. 9A and 9B). Without being limited by theory, follistatin may lead to inhibition of circulating activin A and myostatin, thereby causing an increase in lean muscle mass. Finally, the major organs were resected and weighted upon completion of the study. The data showed no significant changes in heart, liver, spleen, and kidney weight (FIG. 9C), indicating that the follistatin therapy was selective for skeletal muscle tissue. Thus, the compositions and methods disclosed herein facilitate enhanced lean muscle mass without resulting in cardiac hypertrophy, which can lead to decreases in cardiac output and function, eventually causing death.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

What is claimed is:

1. An mRNA polymer complex comprising

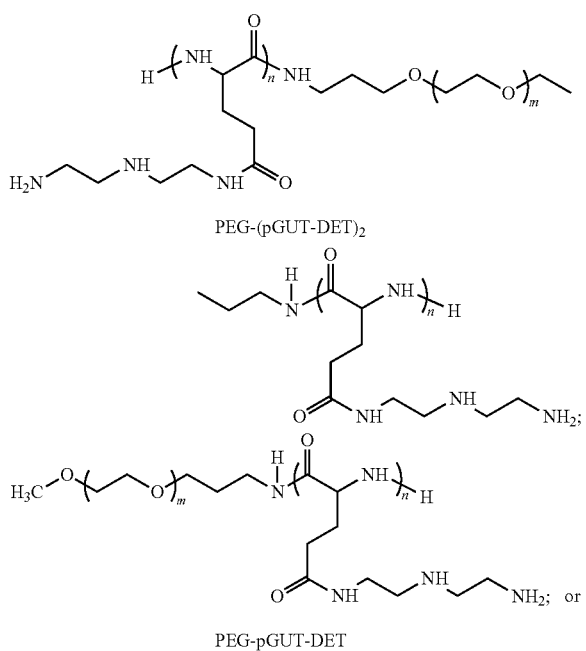

PEG-(pGUT-DET)₂

PEG-pGUT-DET a salt thereof,
wherein m is the number of ethylene oxide groups in the PEG polymer, and n is the number of glutamic acid groups, electrostatically complexed to an mRNA molecule that encodes a desired protein.

2. The complex of claim 1, wherein the mRNA molecule encodes a follistatin protein.

3. The complex of claim 1, wherein the mRNA molecule:
(a) encodes a follistatin protein comprising an amino acid sequence at least 95% identical to the amino acid sequence set forth in SEQ ID NO: 1, SEQ ID NO: 2, SEQ ID NO: 3, or SEQ ID NO: 4, or
(b) comprises a nucleic acid sequence at least 85% identical to the nucleic acid sequence set forth in SEQ ID NO: 5, SEQ ID NO: 6, SEQ ID NO: 7, or SEQ ID NO: 8.

4. The complex of claim 3, wherein the mRNA molecule:
(a) encodes a follistatin protein comprising or consisting of the amino acid sequence set forth in SEQ ID NO: 1, SEQ ID NO: 2, SEQ ID NO: 3, or SEQ ID NO: 4, or
(b) comprises or consists of the nucleic acid sequence set forth in SEQ ID NO: 5, SEQ ID NO: 6, SEQ ID NO: 7, or SEQ ID NO: 8.

5. The complex of claim 1 configured for a desired level of mRNA loading and complexation of the polymer and mRNA.

6. The complex of claim 1, wherein the number of polymer nitrogens and number of mRNA phosphates provide an N/P ratio of about 4.

7. The complex of claim 1, wherein the polymer further comprises NHS-activated 5 kDa polyethylene glycol (PEG) molecules.

8. The complex of claim 1, wherein the polymer further comprises a second block polyethylene glycol (PEG) molecules, wherein the PEG molecules are 2, 5, and/or 12 kDa.

9. The complex of claim 1 configured for delivery to or uptake by hepatic cells.

10. A method of treating a subject in need of augmented muscle growth, comprising administering to the subject a therapeutically effective amount of the complex of claim 2.

11. The method of claim 10, wherein the complex administered subcutaneously, intravenously, and/or intramuscularly.

12. The method of claim 10, wherein the complex is administered every 3 days.

13. The method of claim 10, further comprising assessing toxicity and/or inflammation after administration.

14. The method of claim 10, further comprising selecting the subject in need of augmented muscle growth.

15. The method of claim 10, wherein the subject has acute or chronic muscle atrophy and/or a muscle-wasting disease and administering the complex treats the muscle atrophy and/or the muscle-wasting disease.

16. The method of claim 10, wherein the subject has sarcopenia, cachexia, cancer, congestive heart failure, renal failure, chronic obstructive pulmonary disease, severe burns, an inflammatory muscle disease, myasthenia gravis, neuropathy, polio, multiple sclerosis, anorexia nervosa, human immunodeficiency virus, acquired immune deficiency syndrome, osteomalacia, herniated disk, hypercalcemia, kwashiorkor, Creutzfeldt-Jakob disease, bovine spongiform encephalopathy, diabetes, amyotrophic lateral sclerosis, necrotizing vasculitis, abetalipoproteinemia, malabsorption syndrome, legg-calve-perthes disease, muscular dystrophy, polymyositis, Guillain-Barre syndrome, and/or osteoarthritis and/or has been exposed to a zero-gravity environment.

17. The method of claim 10, wherein the subject is human.

18. A method of slowing the loss of, increasing, and/or maintaining lean muscle mass in a subject, comprising administering to a subject an effective amount of the mRNA complex of claim 2.

19. The mRNA polymer complex of claim 1, wherein the polymer comprises

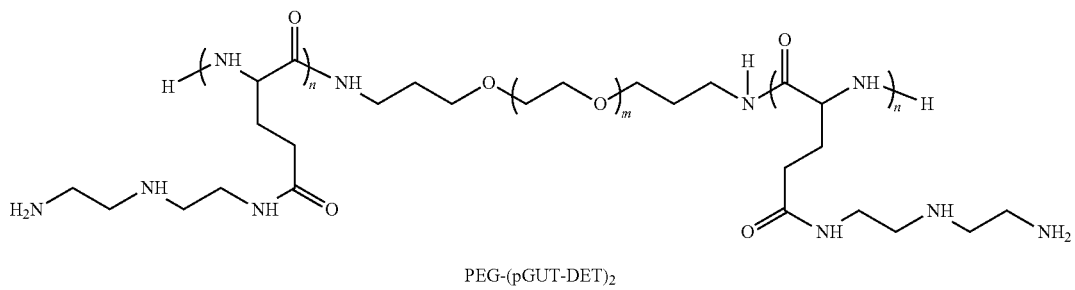

PEG-(pGUT-DET)₂ or a salt thereof, wherein m is the number of ethylene oxide groups in the PEG polymer, and n is the number of glutamic acid groups.
20. The mRNA polymer complex of claim 1, wherein the polymer comprises
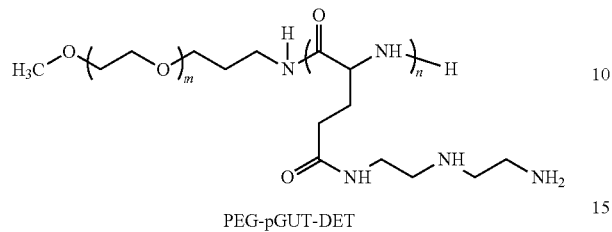
PEG-pGUT-DET
or a salt thereof, wherein m is the number of ethylene oxide groups in the PEG polymer, and n is the number of glutamic acid groups.
* * * * *